United States Patent [19]

Chalom et al.

[11] Patent Number: 5,342,970

[45] Date of Patent: Aug. 30, 1994

[54] HYDROSOLUBLE COUMARIN DERIVATIVES, THEIR PREPARATION AND THEIR USE AS AN ENZYME SUBSTRATE OR FOR THE PREPARATION OF SUCH SUBSTRATES

[75] Inventors: Joseph Chalom, Paris; Christine Griffoul, Rosny Sous Bois; Michel Tod, Margerrey; Stéphane Reveilleau, Paris, all of France

[73] Assignee: Laboratoires Eurobio, France

[21] Appl. No.: 887,767

[22] Filed: May 22, 1992

[30] Foreign Application Priority Data

May 30, 1991 [FR] France ................ 91 06551

[51] Int. Cl.$^5$ .............................. C07D 311/04
[52] U.S. Cl. .......................................... 549/288
[58] Field of Search .................................. 549/288

[56] References Cited

U.S. PATENT DOCUMENTS

| | | | |
|---|---|---|---|
| 2,654,713 | 10/1953 | Fleck | 549/288 |
| 2,844,594 | 7/1958 | Long | 549/288 |
| 3,784,600 | 1/1974 | von Strandtmann et al. | 260/343.2 R |
| 3,985,772 | 10/1976 | Scheuermann et al. | 549/288 |
| 4,421,922 | 12/1983 | Miller et al. | 549/313 |
| 4,540,808 | 9/1985 | Greth | 560/178 |
| 4,777,269 | 10/1988 | Scheper et al. | 549/288 |
| 4,918,200 | 4/1990 | Arkles | 549/288 |
| 5,055,594 | 10/1991 | Mize | 549/288 |
| 5,098,820 | 3/1992 | McManus | 549/288 |

FOREIGN PATENT DOCUMENTS

| | | | |
|---|---|---|---|
| 00063 | 12/1978 | European Pat. Off. | 549/288 |
| 0067409 | 12/1982 | European Pat. Off. | |
| 0076379 | 4/1983 | European Pat. Off. | |
| 53-108974 | 9/1978 | Japan | 549/288 |
| WO80/02295 | 10/1980 | PCT Int'l Appl. | |

OTHER PUBLICATIONS

Knyazev, et al., "Spirocyclic Meisenheimer complexes XXVII . . . " Zh. Org. Khim 27(8) 1727-33 (1980).
Chemical Abstracts Service (of "R"); CA116(15) 151613s 1991.
Patent Abstracts of Japan, vol. 9, No. 188 (C-295) 8 1911] Aug. 3, 1985-JP-A-60-56985 (Sankyo K. K.) Apr. 2, 1985.
Chemical & Pharmaceutical Bulletin, vol. 25, No. 2, Feb. 1977, Tokyo, Japan, pp. 362-363; Yuichi Kanaoka et al.: "A New Fluorogenic Substrate for Aminopeptidase".
Chemical & Pharmaceutical Bulletin, vol. 36, No. 9, Sep. 1988, Tokyo, Japan, pp. 3496-3502; Eisuke Sato et al.: "New Water-Soluble Fluorogenic Amine".
Chemical Abstracts, vol. 112, No. 16, Apr. 16, 1990, Columbus, Ohio, Abstract No. 151038A; M. Tod et al.: "Chromotographic and Luminescence Properties of A 7-Aminocoumarin Derivative with Peroxyoxalate Chemiexcitation".

Primary Examiner—Johann Richter
Assistant Examiner—Catherine S. Kilby Scalzo
Attorney, Agent, or Firm—Pearne, Gordon, McCoy & Granger

[57] ABSTRACT

The invention relates to hydrosoluble coumarin derivatives. These derivatives comply with the formula:

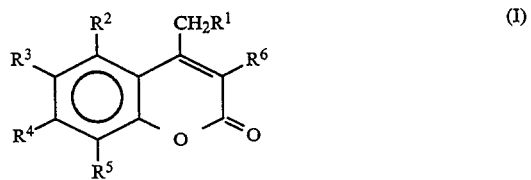

in which $R^1$ represents

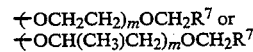

with m=1 to 30 and in which $R^7$ can be a hydrogen atom or various groups, $R^2$ to $R^6$ can be different substituents, particularly substituents making it possible to introduce into the derivative an appropriate group as the enzyme substrate or for the synthesis of enzyme substrates.

8 Claims, 20 Drawing Sheets

HYDROSOLUBLE COUMARIN DERIVATIVES, THEIR PREPARATION AND THEIR USE AS AN ENZYME SUBSTRATE OR FOR THE PREPARATION OF SUCH SUBSTRATES

The present invention relates to novel hydrosoluble coumarin derivatives and to their preparation process from novel β-ketonic esters having a hydrophilic group.

Coumarins are an important family of molecules having very varied applications.

Thus, apart from fields such as pharmacology where they can serve as anticoagulants, coumarins are widely used for their optical properties (fluorescence and chemiluminescence), e.g. as dyes for lasers, fluorescent products for optics, products for the synthesis of enzyme substrates used in medical diagnosis and biological molecule markers, also usable in the field of medical diagnosis.

However, for these various applications, coumarins suffer from the disadvantage of a solubility in water, or in hydrophilic solvents such as alcohols and even in mixed solvents (organic solvent-water mixture) which is mediocre or poor, which reduces their performance characteristics and their use possibilities.

In the case of the preparation of an enzyme substrate, usually a chemical combination is formed between a) a dye or a fluorescent product and b) a biochemical molecule such as an amino acid, a peptide, a sugar or a phosphoric acid molecule. The thus formed substrate must have the following properties:

1°) the dyeing or fluorescence characteristics of a) must be cancelled out or very seriously reduced in the substrate,
2°) the substrate must be able to react with specific enzymes to undergo a cleaving,
3°) the cleaving must regenerate the dyeing or fluorescent product a) and thus restore the colour or fluorescence and
4°) this restoration must be proportional to the enzyme quantity used so that the substrates can be used for enzyme dosing.

Among the known coumarin derivatives use has hitherto been made for the preparation of enzyme substrates of 7-amino-4-methyl coumarin, 7-amino-coumarin-4-methane sulphonic acid and 7-amino-4-trifluoromethyl coumarin, as described in Chem. Pharm. Bull., vol.25, 1977, pp.362/3, Chem. Pharm. Bull., vol.36, 1988, pp.3496–3502 and WO 80/02295.

Coupled with leucine, 7-amino-4-methyl coumarin can e.g. be used as a substrate for leucine aminopeptidase, This coumarin is very interesting because it is very fluorescent with a maximum fluorescence intensity approximately 14 times higher than that of the amines conventionally used as the substrate, such as β-naphthyl amine. Moreover, there is a significant fluorescence intensity difference between aminocoumarin and the corresponding amide substrate.

However, it is slated in Chem. Pharm. Bull., vol.36, pp.3496–3502, 1988 that it is necessary to use with said aminocoumarin a mixture of water and organic solvent such as dimethylsulphoxide due to its inadequate solubility in water, which is a disadvantage because numerous enzymes such as encephalinase are sensitive to organic solvents. In addition, the presence of an organic solvent makes the dosing procedure more difficult.

To improve the solubility in water of said coumarin, the methyl group in the 4 position has been replaced by the more hydrophilic sulphonic methane group. However, the synthesis of the latter aminocoumarin is relatively complicated and is also unsuitable for several enzymes.

The present invention specifically relates to novel hydrosoluble coumarin derivatives obviating the aforementioned disadvantages as a result of the presence in the 4 position of the coumarin nucleus of a polyether chain giving them an improved solubility in water, but without modifying their fluorescent or dyeing properties.

These coumarin derivatives comply with the formula:

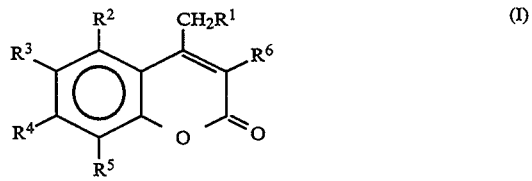

in which
1) $R^1$ represents a radical complying with the formulas

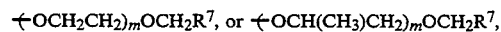

in which m is an integer from 1 to 30 and $R^7$ represents a hydrogen atom, a halogen atom, OH, $OR^8$, SH, $SR^8$, COOH, $COOR^9$, $CONHR^8$, $CONR^8R^{10}$, $CONHNH_2$,

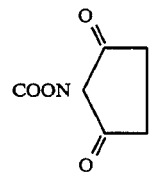

$NH_2$, $NHR^8$, $NR^8R^{10}$, $SO_3H$, $SO_3R^9$, or an alkyl, alkoxy or aryl radical, which is unsubstituted or substituted by at least one substituent chosen from among the halogen atoms, phenyl radical, $CF_3$, OH, $OR^8$, SH, $SR^8$, COOH, $COOR^9$, $NH_2$, $NHR^8$, $NR^8R^{10}$, $SO_3H$ and $SO_3R^9$, in which $R^8$ is alkyl or aryl radical, $R^9$ an alkyl or aryl radical, $NH_4$ or $M_{1/v}$ with M being a valency metal v and $R^{10}$ is an alkyl or aryl radical or $R^8$ and $R^{10}$ can together form a saturated or unsaturated hydrocarbon cycle optionally incorporating a heteroatom chosen from among O, S and N, 2) $R^2$, $R^3$, $R^4$ and $R^5$, which can be the same or different, represent a hydrogen atom, a halogen atom, $NH_2$, $NHR^8$, $NR^8R^{10}$, $NHR^{11}$, $NR^8R^{11}$, SH, $SR^8$, $SR^{11}$, OH, $OR^8$, $OR^{11}$ with $R^8$ and $R^{10}$ having the meaning given hereinbefore and $R^{11}$ representing an acyl radical derived from a compound chosen from among protected or unprotected amino acids, protected or unprotected peptides, carboxylic acids and fatty acids, the radical $PO_3R_2$ with R being a hydrogen atom or an alkyl radical, or a radical derived from a sugar, or an alkoxy or alkyl radical, which is unsubstituted or substituted by at least one substituent chosen from among the halogen atoms, OH, OR$^8$, SH, SR$^8$, COOH, COOR$^9$, NH$_2$, NHR$^8$, NR$^8$R$^{10}$, SO$_3$H, SO$_3$R$^9$, SR$^{11}$, OR$^{11}$, CF$_3$, NHR$^{11}$ and NR$^8$R$^{11}$ with R$^8$, R$^9$, R$^{10}$ and R$^{11}$ having the meanings given hereinbefore, or 3) R$^2$ and R$^3$, R$^3$ and R$^4$ or R$^4$ and R$^5$ together form a saturated or unsaturated cyclic nucleus with 5 to 8 carbon atoms, or a heterocyclic nucleus having at least one heteroatom chosen from among N, O and S, or 4) R$^3$, R$^4$ and R$^5$ form together with the phenyl nucleus which they are linked a polycyclic nucleus having three condensed cycles and optionally having one or more heteroatoms chosen from among N, O and S, or 5) R$^2$, R$^3$ and R$^4$ form with the phenyl nucleus to which they are linked a polycyclic nucleus having three condensed cycles and optionally one or more heteroatoms chosen from among N, O and S and 6) R$^6$ represents a hydrogen atom, a halogen atom, COOH, COOR$^9$ with R$^9$ having the meaning given hereinbefore, or an alkyl radical, which is unsubstituted or substituted by at least one substituent chosen from among the halogen atoms, OH, SH, COOH, COOR$^9$, OR$^8$, SR$^8$, SO$_3$H and SO$_3$R$^9$ with R$^8$ and R$^9$ having the meaning given hereinbefore.

In the formula given hereinbefore, the terms alkyl or alkoxy radical designate straight or branched-chain radicals generally having 1 to 10 and preferably 1 to 5 carbon atoms.

The term aryl radical designates the radicals derived from aromatic hydrocarbons such as benzene and naphthalene. As an example of such radicals reference can be made to the phenyl and naphthyl radicals.

The term hydrocarbon cycle refers to saturated or unsaturated cyclic hydrocarbons having 3 to 10 carbon atoms.

When they have one or more heteroatoms, it can e.g. be piperidine, pyridine, piperazine, pyrrole, furan, pyran or morpholine.

The amino acids used for R$^{11}$ can be natural amino acids and in particular those used for forming substrates or enzymes, These acids can be protected at the free amine function (e.g. by. carbobenzoxy, fluorenylmethoxycarbonyl and t-butoxycarbonyl groups). Inclusion is also made of an amino acid derivative, which is pyroglutamic acid.

The peptides used are formed from several amino acids and in particular natural amino acids. In these peptides, dextrogyratory or synthetic amino acids can be integrated into the chain. The peptides can also be modified at the amine function which has remained free (e.g. by carbobenzoxy, fluorenyhlmethoxycarbonyl, t-butoxycarbonyl and succinyl groups.

The sugars used for R$^{11}$ can be monosaccharides such as glucose, mannose and galactose. If R$^{11}$ is a carbobenzoxyarginyl radical a substrate of trypsin is obtained. If R$^{11}$ is a pyroglutamyl radical a substrate of pyroglutamyl amino peptidase is obtained. If R$^{11}$ is a γ-glutamyl radical, a γ-glutamyl transferase substrate is obtained.

When R$^2$ and R$^3$, R$^3$ and R$^4$ or R$^4$ and R$^5$ form a cycle, it can be in the form of hydrocarbon cycles and heterocycles referred to hereinbefore.

When R$^2$, R$^3$ and R$^4$ or R$^3$, R$^4$ and R$^5$ form together with the phenyl radical a polycyclic nucleus optionally having one or more heteroatoms, it can e.g. be the following nucleus:

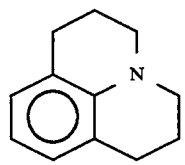

The metals M representing R$^9$ can e.g. be alkali metals such as sodium.

In the above formula (I) the presence of the radical R$^1$ having a polyether chain makes it possible to give the coumarin derivative hydrosolubility properties, whilst the presence of at least one substituent R$^2$, R$^3$, R$^4$ or R$^5$ makes it possible to give the derivatives other properties, e.g. the reinforcement of the fluorescent and chemiluminescent properties of coumarin, the formation of an enzyme substrate or making possible the synthesis of enzyme substrates usable for enzyme dosing or determination.

Moreover, according to a first embodiment of the invention, at least one of the R$^2$, R$^3$, R$^4$ and R$^5$ represents NH$_2$, NHR$^8$, NHR$^{11}$, NR$^8$R$^{11}$, SH, OH, SR$^{11}$ or OR$^{11}$ with R$^8$ and R$^{11}$ having the meanings given hereinbefore.

Preferably, in this first embodiment of the invention, one only of R$^2$, R$^3$, R$^4$ and R$^5$ represents NH$_2$, NHR$^8$, NHR$^{11}$, NR$^8$R$^{11}$, SH, OH, SR$^{11}$ or OR$^{11}$. In this case, the others generally represent a hydrogen atom.

Once again in preferred manner, R$^2$, R$^3$ and R$^5$ represent a hydrogen atom and R$^4$ represents one of the aforementioned substituents.

This first embodiment is particularly appropriate for the use of coumarin derivatives as enzyme substrates for enzyme dosing or determination or as intermediates for enzyme substrate preparation.

Thus, when R$^2$, R$^3$, R$^4$ or R$^5$ represents a group chosen from among NH$_2$, NHR$^8$, NHR$^{11}$, SH and OH, e.g. NH$_2$ or OH, it is easily possible to couple the coumarin derivative with an appropriate compound for producing an enzyme substrate by reacting the compound with this substituent group. These derivatives constitute very interesting intermediates because, on the basis of a single derivative, it is possible to produce a range of enzyme substrates by reacting said product with appropriate compounds.

When R$^2$, R$^3$, R$^4$ or R$^5$ represents NHR$^{11}$, NR$^8$R$^{11}$, SR$^{11}$ or OR$^{11}$, R$^{11}$ is chosen so as to give the coumarin derivative the property of being an enzyme substrate. As an example of such substrates, reference can be made to the coumarin derivative of formula (I), in which R$^4$ represents NHR$^{11}$ with R$^{11}$ being the radical derived from L-leucine of formula:

$$(CH_3)_2CH-CH_2-C(NH_2)-C(O)-,$$

which constitutes a leucine aminopeptidase substrate.

As examples of other substrates, reference can be made to coumarin derivatives of formula (I), in which R$^4$ represents NHR$^{11}$ with R$^{11}$ being chosen from among the radicals of formula:

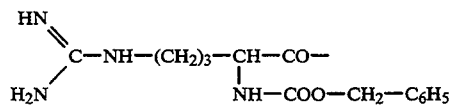

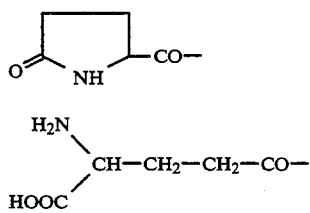

As examples of coumarin derivatives usable as intermediates for the preparation of optionally polypeptidic substrates, reference can be made to the coumarin derivatives of formula (I), in which $R^4$ represents $NH_2$, OH or a radical chosen from among those of formula:

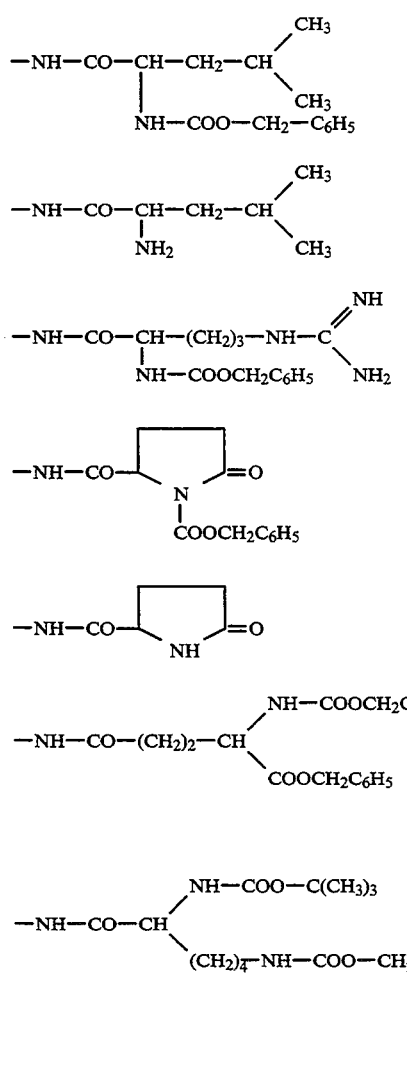

Generally, in this first embodiment of the invention, $R^6$ represents a hydrogen atom, but it could also represent a substituent making it possible to further improve the hydrosolubility or fluorescence.

According to a second embodiment of the invention, more particularly aimed at coumarin derivatives used as a fluorescent product or dye, at least one of $R^2$, $R^3$, $R^4$, and $R^5$ represents $NH_2$, $NHR^8$, $NR^8R^{10}$, OH, $OR^8$, SH, $SR^8$ or a substituted or unsubstituted alkyl radical, with a view to reinforcing the fluorescent or dyeing properties or the hydrosolubility of coumarin.

in a variant of said second embodiment $R^2$, $R^3$ and $R^4$ or $R^3$, $R^4$ and $R^5$ form together with the phenyl nucleus with which they are linked, a polycyclic nucleus having three condensed cycles and a nitrogen atom, which also makes it possible to reinforce the fluorescent or dyeing properties.

In the two embodiments of the invention, $R^1$ advantageously represents $-(OCH_2CH_2)_mOCH_2R^7$.

For example, $R^7$ can represent a hydrogen atom, $COOR^9$ or COOH.

The coumarin derivatives according to the invention can be prepared by a conventional process using the Pechman reaction starting from novel β-ketonic esters having the hydrophilic group $R^1$.

The invention also relates to these novel β-ketonic esters complying with the formula:

in which $R^1$ and $R^6$ have the meanings given hereinbefore and $R^{12}$ represents an alkyl, aryl or cycloalkyl radical. Preferably $R^6$ is a hydrogen atom.

The alkyl or aryl radicals representing $R^{12}$ can be of the same type as those described hereinbefore in connection with formula (I). The cycloalkyl radicals generally have 5 to 7 carbon atoms.

Preferably, use is made for $R^{12}$ of an alkyl radical having 1 to 4 carbon atoms, e.g. the ethyl or methyl radical.

These β-ketonic esters can be prepared by a conventional process from acids of formula $R^1-CH_2-COOH$.

The preparation process of these β-ketonic esters e.g. comprises the following stages:

1°) transforming an acid of formula $R^1-CH_2-COOH$, in which $R^1$ has the meaning given hereinbefore, into the corresponding acid chloride or imidazolide, 2°) reacting the acid chloride or imidazolide with an ester of formula:

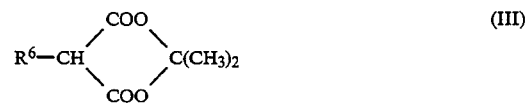

for forming an acylated derivative and

3°) reacting the acylated derivative with an alcohol of formula $R^{12}OH$ for obtaining the β-ketonic ester of formula (II).

The starting acids $R_1-CH_2-COOH$ are commercial products or can be prepared by conventional processes.

The ester of formula (III) is commercially available (Meldrum acid) or can be prepared by a conventional process starting with Meldrum acid or a diethyl malonate and carrying out two successive substitutions on the malonic $CH_2$.

For preparing the coumarin derivatives of formula (I) of the invention, the β-ketonic ester of formula (II) is reacted with a phenol of formula:

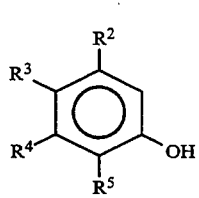

(IV)

in which $R^2$, $R^3$, $R^4$ and $R^5$ have the meanings given hereinbefore.

This condensation reaction (Pechmann reaction) can be performed in ethanol in the presence of an acid catalyst such as $H_2SO_4$, $HCl$, $CF_3COOH$ or their salts, e.g. aluminium chloride, zinc chloride or tin chloride.

When one of the $R^2$, $R^3$, $R_4$, $R^5$ is a substituent of type $NHR^{11}$, $NR^8R^{11}$, $SR^{11}$ or $OR^{11}$, preference is generally given to the initial preparation of the coumarin derivative in which said substituent is $NH_2$, $NHR^8$, $SH$ or $OH$ and transforming the same into the desired substituent by reacting with a compound able to supply $R^{11}$.

Thus, when $R^{11}$ is a radical derived from an amino acid, it is possible to react the amino acid (generally protected on its amine function) or the fatty acid with the coumarin derivative having a substituent $NH_2$ or $NHR_8$, $SH$ or $OH$ in order to form a bond of the peptide or ester type.

The phenols used for the reaction can be prepared by conventional processes or are commercial products.

The use of the β-ketonic esters of formula (II) described hereinbefore is of interest because it makes it possible to directly include on the coumarin nucleus a chain of the polyether type without any intermediate use of an unstable group, e.g. of the type CO—NH, which can be cleaved by certain enzymes.

As has been shown hereinbefore, the coumarin derivatives corresponding to the first embodiment of the invention having a $R^{11}$ group on one of the $R^2$, $R^3$, $R^4$ and $R^5$, can be used as enzyme substrates in an enzyme determination process. For such determinations or doses, it is possible to use the derivative as it is, or in the form of an addition salt to the acids, e.g. in the form of hydrochloride, hydrobromide or trifluoroacetate.

In order to carry out such a determination, a solution of a coumarin derivative of formula (I) is firstly prepared in which $R_2$, $R^3$, $R^4$ or $R^5$ represents $NHR^{11}$, $NR^8R^{11}$, $SR^{11}$ or $OR^{11}$ and in which $R^{11}$ can fulfil the substrate function for the enzyme to be determined or dosed, followed by the determination of the fluorescence intensity of the thus prepared coumarin derivative solution. To the said solution is then added a sample of the enzyme solution to be dosed and following a given period of e.g. 6 minutes, the fluorescent intensity of the solution is determined. This is followed by the determination of the enzyme concentration of the solution to be dosed on the basis of a standard curve giving the fluorescence intensity variations as a function of the enzyme concentration, which has been prepared from samples having known enzyme concentrations by carrying out dosings under the same conditions.

During this dosing or determination, the enzyme present in the sample to be dosed hydrolyzes the enzyme substrate regenerating the coumarin derivative, e.g. the derivative of formula (I), with $R^4$ representing $NH_2$, $NHR_8$, $OH$ or $SH$, which has a much greater fluorescence than the derivative in which $R^4$ represents $NHR^{11}$, $SR^{11}$, $NR^8R^{11}$ or $OR^{11}$.

The restoration of the fluorescent activity is proportional to the enzyme quantity of the sample.

Other features and advantages of the invention can be gathered from the study of the following examples given in an illustrative and non-limitative manner with reference to the attached drawing.

EXAMPLE 1

Figure 1:
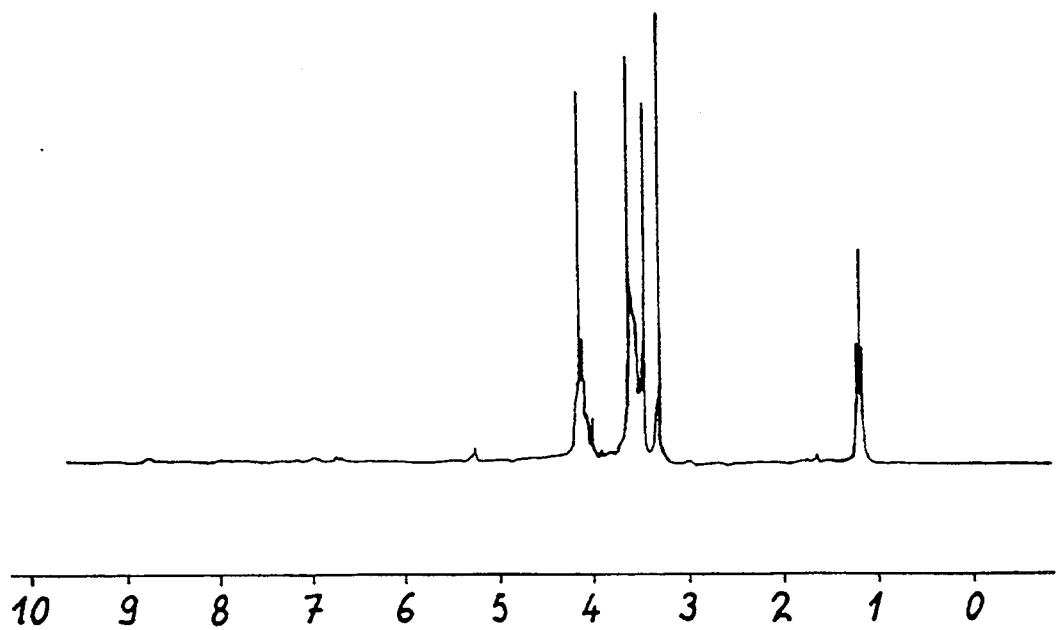
FIGS. 1, 2, 4, 7, 10, 12, 15, 16, 18, 20, 23, 26, 30, 33, 34, 35 and 37 are NMR spectra of compounds according to the invention.

Preparation of 3,6,9-trioxadecanoyl ethyl acetate (compound 1)

This compound is a β-ketonic ester of formula (II) with $R^1 = (OCH_2CH_2)_2OCH_3$ $R^{12} = C_2H_5$.

In a first container preparation takes place of an anhydrous solution of 29 g of 3,6,9-trioxadecanoic acid (0.16 mole) in 400 ml of dichloromethane. Accompanied by stirring, into said solution are then introduced 28.3 g (0.174 mole) of carbonyl diimidazole and stirring is continued for 2 hours.

Into a second container are introduced 24.65 g of Meldrum acid in 400 ml of anhydrous dichloromethane, followed by cooling to $-50°$ C. and the addition of 12.9 g of pyridine in 24 ml of dichloromethane.

Whilst keeping the second container at $-5°$ C., over a period of 30 min and protected from light, introduction takes place of the solution of the first container, followed by heating to 40° C. for 15 min.

This is followed by the addition of 165 ml of ice water, accompanied by cooling and then leaving to settle. The organic phase is then washed with 120 ml of 2.5N HCl and then with 120 ml of saturated saline solution, followed by evaporation to dryness.

The residue is then taken up in 500 ml of anhydrous ethanol and refluxing takes place for 150 min. This is followed by vacuum evaporation, distillation and the obtaining in this way of 12.1 g of compound 1, which corresponds to a 30% yield.

The compound has the following characteristics:
1°) Boiling point under 54 Pa: 140°-145° C.
2°) Thin layer chromatography (TLC) of fluorescent silica using as the eluent a butanol/acetic acid/water mixture (60:20:20): Rf=0.7, developed under ultraviolet at 254 nm, with iodine vapours and 2,4 DNPH.
3°) NMR (nuclear magnetic resonance) spectrum.

Figure 2:
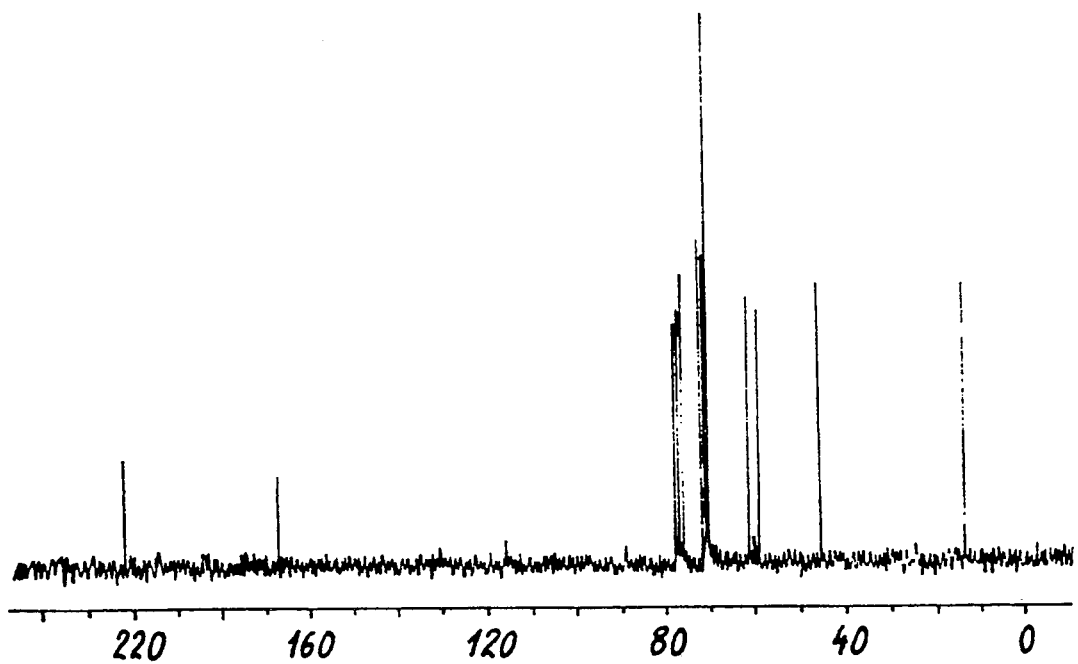

FIGS. 1 and 2 respectively show the NMR spectrum of the proton and carbon 13. These spectra confirm the structure of the product.

EXAMPLE 2

Preparation of 10-carboxybenzyl-3,6,9-decanoyl ethyl acetate (compound 2)

This compound is a β-ketonic ester complying with formula (II) with $R^1 = (OCH_2CH_2)_2OCH_2$—COO—$CH_2$—$C_6H_5$,
$R^{12}$ = ethyl,
$R^6$ = H.

For this preparation, the starting product is 3,6,9-trioxaundecane-1,11-dioic acid, which is transformed into monobenzyl ester by coupling in the presence of dicyclohexyl carbodiimide. The monobenzyl ester is then transformed into β-ketonic ester by using the same operating procedure as in example 1.

a) Preparation of the monobenzyl ester of 3,6,9-trioxaundecane-1,11-dioic acid (compound 3) of formula

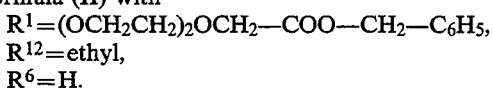

10.8 g of benzyl alcohol and 0.7 g of amino pyridine (DMAP) are introduced onto an anhydrous solution of 88.9 g of 3,6,9-trioxaundecane-1,11-dioic acid in 700 ml of $CH_2Cl_2$. Whilst cooling to 5° C., 20.6 g of dicyclohexyl carbodiimide (DCCI) are introduced into 40 ml of anhydrous dichloromethane. Stirring takes place for 2 h at ambient temperature. The precipitate formed is then filtered. The filtrate is washed with 150 ml of 1N hydrochloric acid, 150 ml of water and then twice with 200 ml of 0.8N sodium bicarbonate. The bicarbonate solution is acidified by adding 3N hydrochloric acid to adjust its pH to 2. It is then extracted with 3 times 150 ml of dichloromethane. The organic extracts are evaporated to dryness and this gives 11.7 g of monobenzyl ester (compound 3), which corresponds to a 38% yield.

The product has the following characteristics:

1°) fluorescent silica thin layer chromatography using as the eluent a mixture of butanol, acetic acid and water (60:20:20) gives a Rf of 0.5, developed under uv at 254 nm and with iodine vapours.

2°) Mass spectrometry (ammonia ionization).

Figure 3:
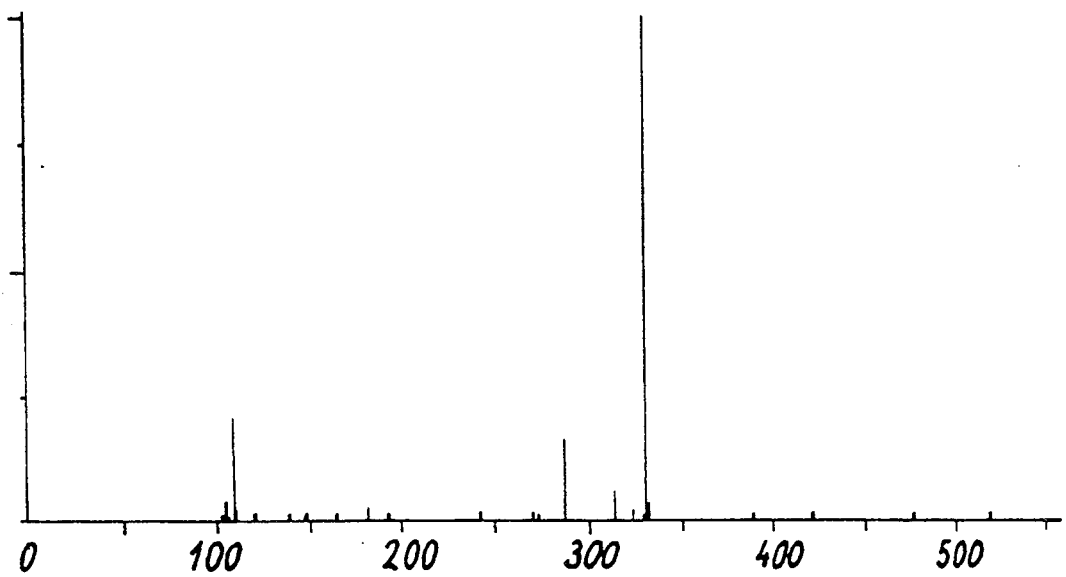
FIGS. 3, 5, 6, 8, 9, 11, 13, 14, 17, 19, 21, 22, 27, 31, 32, 36 and 38 are mass spectra of the compounds according to the invention.

FIG. 3 shows the mass spectrum of this product. The peak at 313 (M+1) and 330 (M+18) confirms the mass of the product, which is 312.

3°) NMR spectrum (200 MHz).

Figure 4:
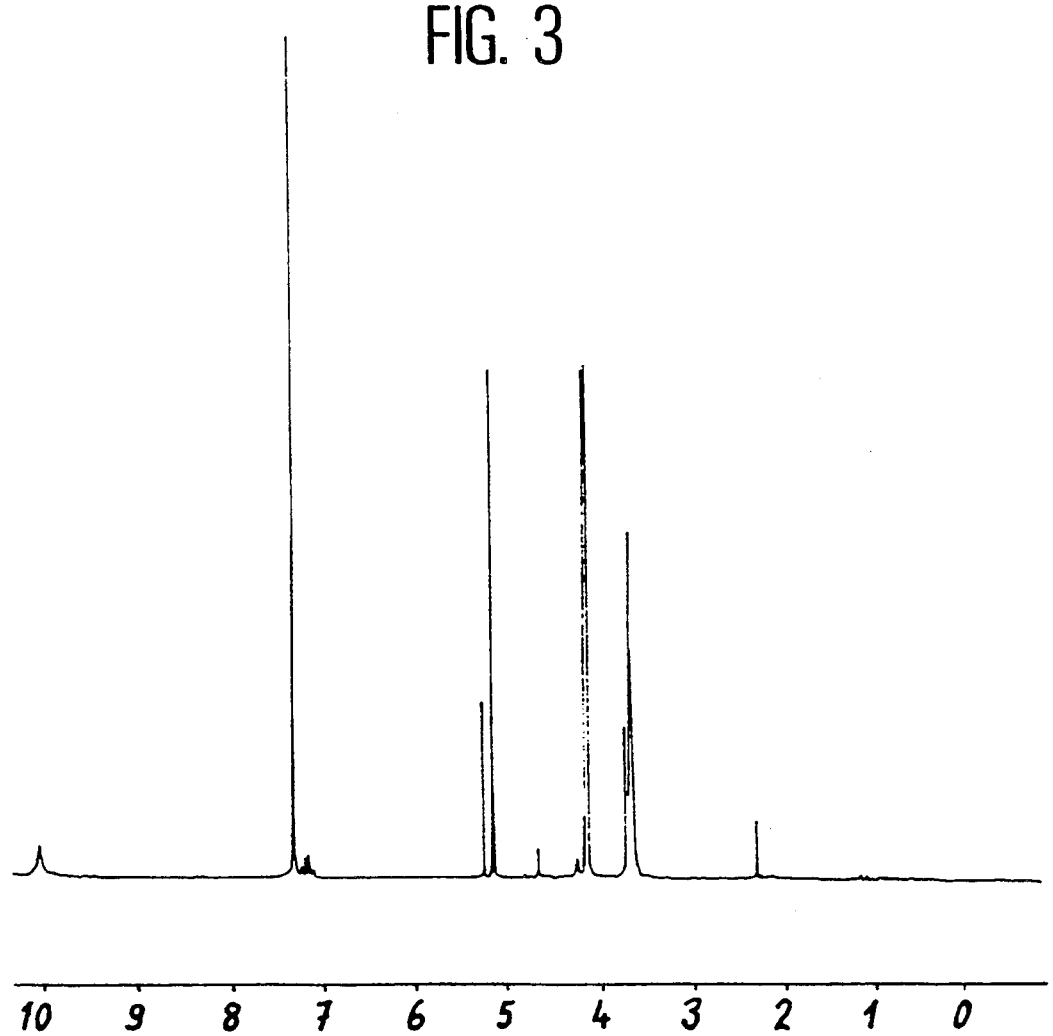

FIG. 4 shows the spectrum of the proton and confirms the structure of the product.

b) Preparation of 10-carboxybenzyl-3,6,9-decanoyl ethyl acetate (compound 2)

In a first container preparation takes place of a solution of 10 g of monobenzyl ester prepared in a) (compound 3) in 16 ml of dichloromethane. This is followed by the introduction, accompanied by stirring, of 5.71 g (0.035 mole) of carbonyl diimidazole and stirring is continued for 2 h.

Into a second container are introduced 5.04 g of Meldrum acid in 16 ml of anhydrous dichloromethane, followed by cooling to −50° C. and the addition of 2.5 g of pyridine in 6 ml of dichloromethane.

Into said second container which is still at −5° C., over a period of 30 min and protected from air, is introduced the imidazolide solution of the first container, followed by heating to 40° C. for 15 min.

Accompanied by cooling, addition takes place of 24 ml of ice water, followed by settling, washing the organic phase with 15 ml of 2.5N HCl and 15 ml of saturated saline solution and evaporation to dryness of the organic phase.

The residue is taken up in 100 ml of anhydrous ethanol, refluxed for 150 min and evaporated in vacuo. Purification takes place on a silica column using as the eluent a mixture of $CH_2Cl_2$/tetrahydrofuran (THF) (90:10). This gives 4.7 g of compound 2 (fractions 22 to 43), which corresponds to a 39% yield.

The product has the following characteristics.

1°) Thin layer chromatography.

Using fluorescent silica $K_6F$ and a butanol-acetic acid-water mixture (60:20:20) as the solvent, a Rf of 0.55 is obtained, developed at 254 nm and 365 nm and with iodine.

2°) Mass spectrometry (chemical ionization with ammonia).

Figures 5, 6:
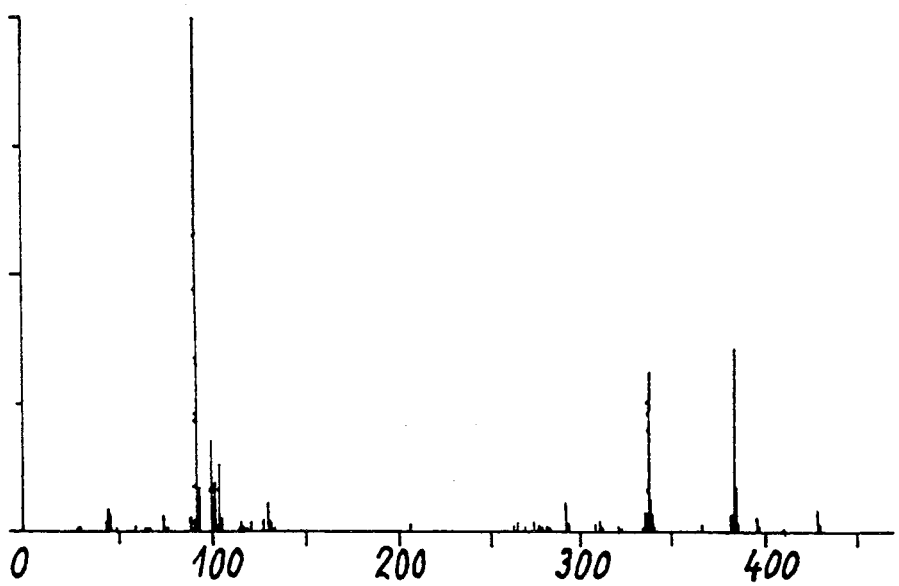

FIG. 5 shows the mass spectrum of compound 2. The peak at M+1=383 confirms the molecular mass of the product (382).

EXAMPLE 3

Preparation of 7-amino-4-(2',5',8'-trioxanonyl)coumarin (compound 4) of formula

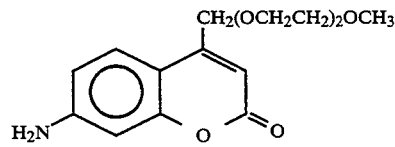

This compound complies with formula (I) with
$R^1 = (OCH_2CH_2)_2OCH_3$
$R^2 = R^3 = R^5 = R^6 = H$, and
$R^4 = NH_2$.

Into a 100 ml round-bottomed flask are introduced 15 g (0.06 mole) of compound 1, 6.6 g (0.06 mole) of 3-aminophenol, 45 ml of absolute ethanol and 9.5 g of zinc chloride. The reaction mixture is heated to boiling, accompanied by stirring, for 24 h and is then poured into a mixture of 800 ml of dichloromethane and 600 ml of water. It is allowed to settle, the aqueous phase is extracted with twice 200 ml of dichloromethane and the combined organic phases are washed with 120 ml of water. Evaporation to dryness takes place. Crystallization takes place in 50 ml of ethyl acetate, followed by the purification of the crude product obtained on a silica column using ethyl acetate as the eluent and recrystallization occurs in ethyl acetate. This gives 2.67 g of compound 4, which corresponds to a 15% yield.

The product has the following characteristics.

1°) TLC (fluorescent silica $K_6F$, ethyl acetate): Rf=0.5 (development at 254 nm, 356 nm, $I_2$).

2°) Mass spectrometry (chemical ionization with ammonia).

FIG. 6 shows the mass spectrum and the peak at M+1=294 confirms the molecular mass of 293.

3°) NMR ( 200 MHz ).

Figure 7:
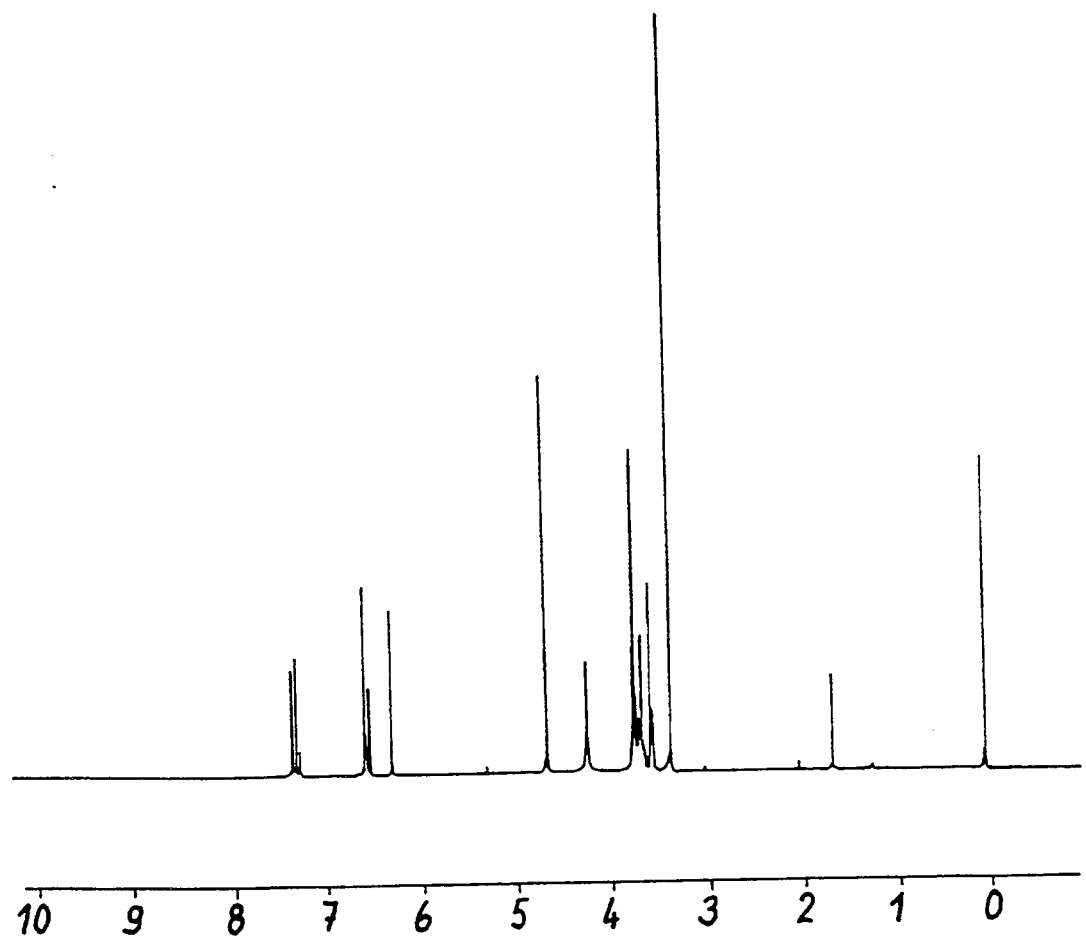

FIG. 7 shows the spectrum of the proton obtained and confirms the structure of the product.

4°) Solubility in water: 0.4 g/l (1.33 mM).

EXAMPLE 4

Preparation of
7-dimethylamino-4-(2',5',8'-trioxanonyl)-coumarin
(compound 5) of formula

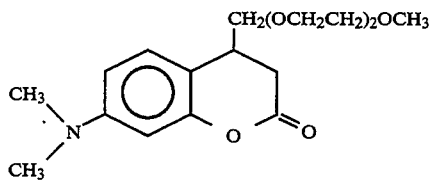

Into a 25 ml Erlenmeyer flask are introduced 2.06 g (15 mmole) of 3-dimethylaminophenol, 3.72 g (15 mmole) of compound 1, 7 ml of absolute ethanol and 2.35 g of zinc chloride.

Boiling takes place, accompanied by stirring, for 24 h and the solution is poured into a mixture of 200 ml of dichloromethane and 150 ml of water. The aqueous phase is extracted with twice 50 ml of dichloromethane and the combined organic phases are washed with 50 ml of water, followed by evaporation to dryness.

The product obtained is purified on a silica column using ethyl acetate as the eluent. This gives 3.36 g of compound 5, which corresponds to a 70% yield, The product has the following characteristics.

1°) TLC (fluorescent silica K$_6$F, ethyl acetate):
 Rf=0.55, developed at 254 nm, 365 nm and with iodine.

2°) Mass spectrum (chemical ionization with ammonia).

Figure 8:
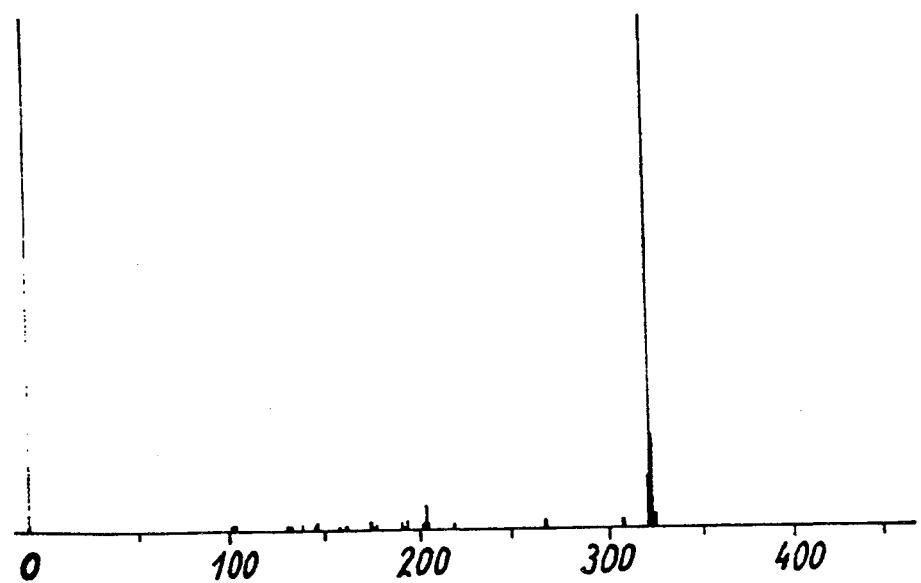

FIG. 8 shows the spectrum obtained and the peak at M+1=322 confirms the molecular mass of 321.

EXAMPLE 5

Preparation of
7-diethylamino-4-(2',5',8'-trioxanonyl)-coumarin
(compound 6) of formula

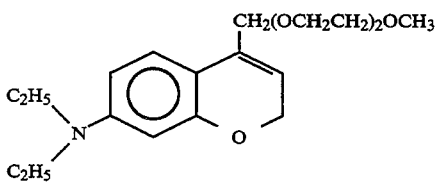

The operating procedure of example 4 is adopted for preparing said compound from compound 1, but using 2.48 g (15 mmole) of 3-diethylaminophenol instead of 2.06 g of 3-dimethylaminophenol, whilst purifying the crude product on a silica column, but using as the eluent CH$_2$Cl$_2$ and then two mixtures CH$_2$Cl$_2$—THF (95:5 and 90:10). This gives 3.1 g of compound 6, which corresponds to a 60% yield.

The product has the following characteristics.

1°) TLC (fluorescent silica K$_6$F, butanol, acetic acid 60:20:20):
 Rf=0.68, developed at 254 nm, 356 nm and with iodine.

2°) Mass spectrum (chemical ionization with ammonia).

Figure 9:
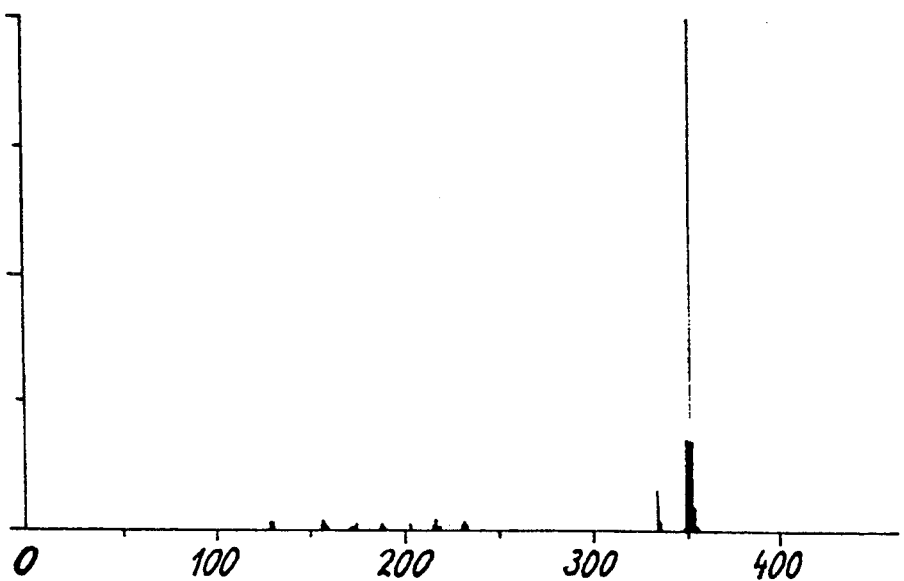

FIG. 9 shows this spectrum and the peak at M+1=350 confirms the molecular mass of 349.

3°) NMR (200 MHz).

Figure 10:
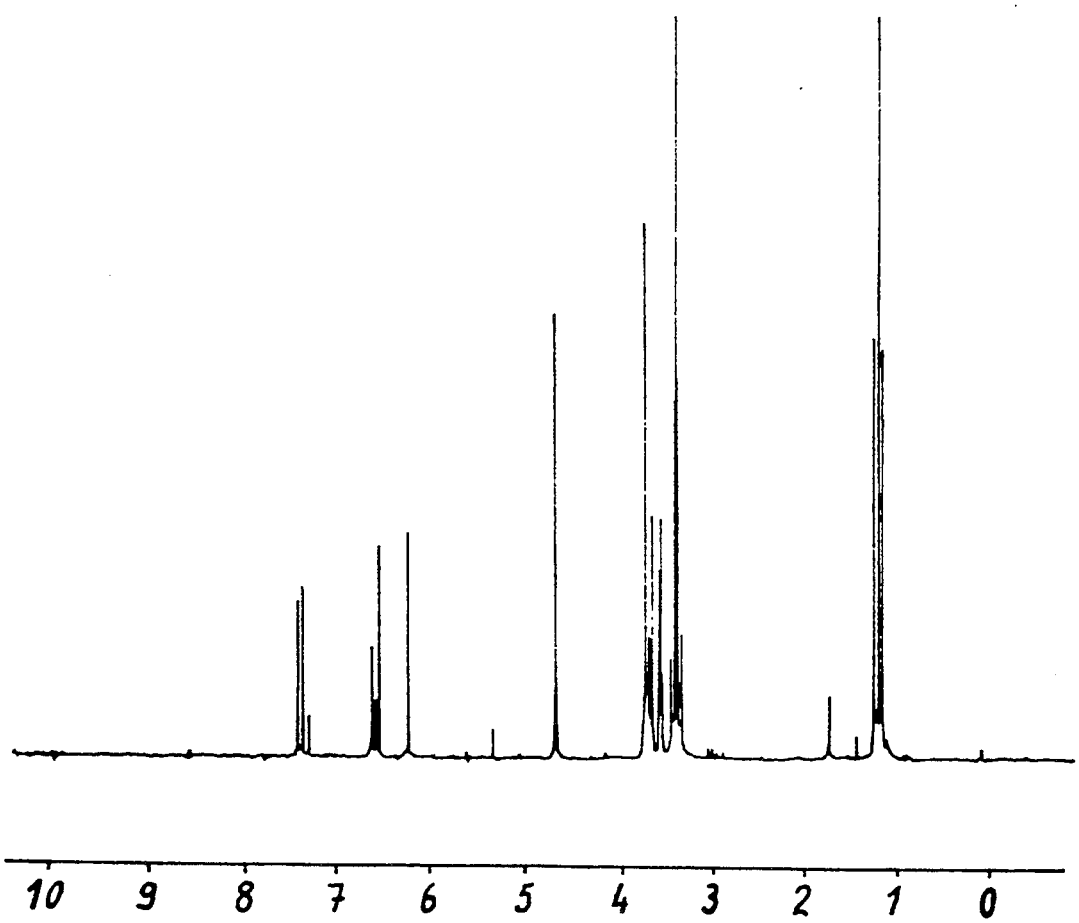

FIG. 10 shows the spectrum of the proton, which confirms the structure of the compound.

EXAMPLE 6

Preparation of
2,3,6,7-tetrahydro-9-(2',5',8'-trioxanonyl)-1H, 5H, 11H-(1)-benzopyrano-(6,7,8-ij)-quinolizinone-11
(compound 7) of formula

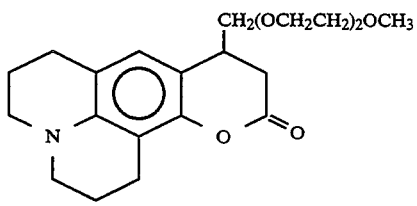

Into a 100 ml round-bottomed flask are introduced 3 g of 8-hydroxyjulolidine, 3.93 g of ethyl 3,6,9-trioxadecanoate, 12 ml of absolute ethanol and 2.49 g of zinc chloride. Heating to boiling takes place accompanied by stirring for 24 h and then the content of the flask is poured into a mixture of 200 ml of dichloromethane and 150 ml of water. The aqueous phase is extracted with twice 50 ml of dichloromethane and the combined organic phases are washed with 50 ml of water and then evaporated to dryness.

The crude product is purified on a silica column using as the eluent CH$_2$Cl$_2$ and then the mixture CH$_2$Cl$_2$—THF (90:10) and the oil obtained is crystallized in water. This gives 3.09 g of compound 7, which corresponds to a 52% yield.

The product has the following characteristics:

1) TLC (fluorescent silica K$_6$F, CH$_2$Cl$_2$—THF, 90:10),
 Rf=0.6, developed at 254 nm, 356 nm and with iodine.

2°) Mass spectrum (chemical ionization with ammonia).

Figure 11:
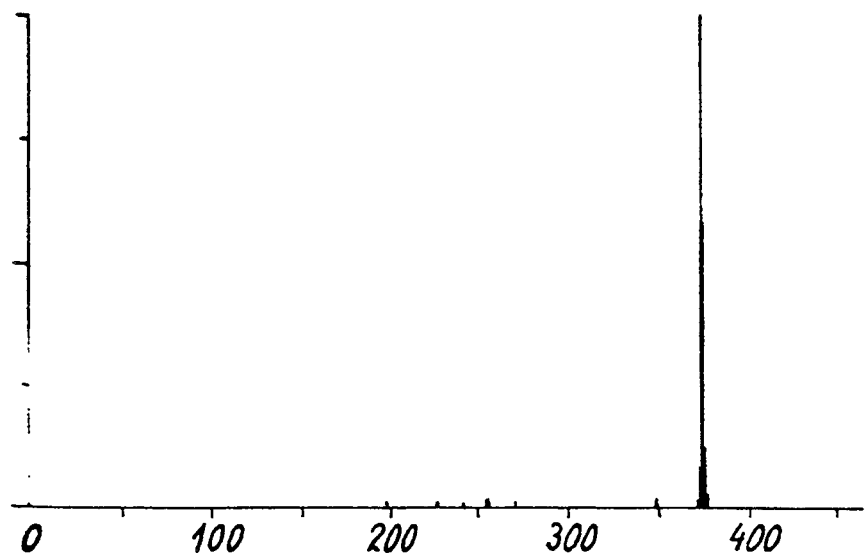

FIG. 11 shows the spectrum obtained, the peak at M+1=374 confirming the molecular mass of 373.

3°) NMR (200 MHz)

4°) Solubility in water: 0.2 g/l.

5°) Solubility in ethanol:water mixture (30:70):3 g/l.

Figure 12:
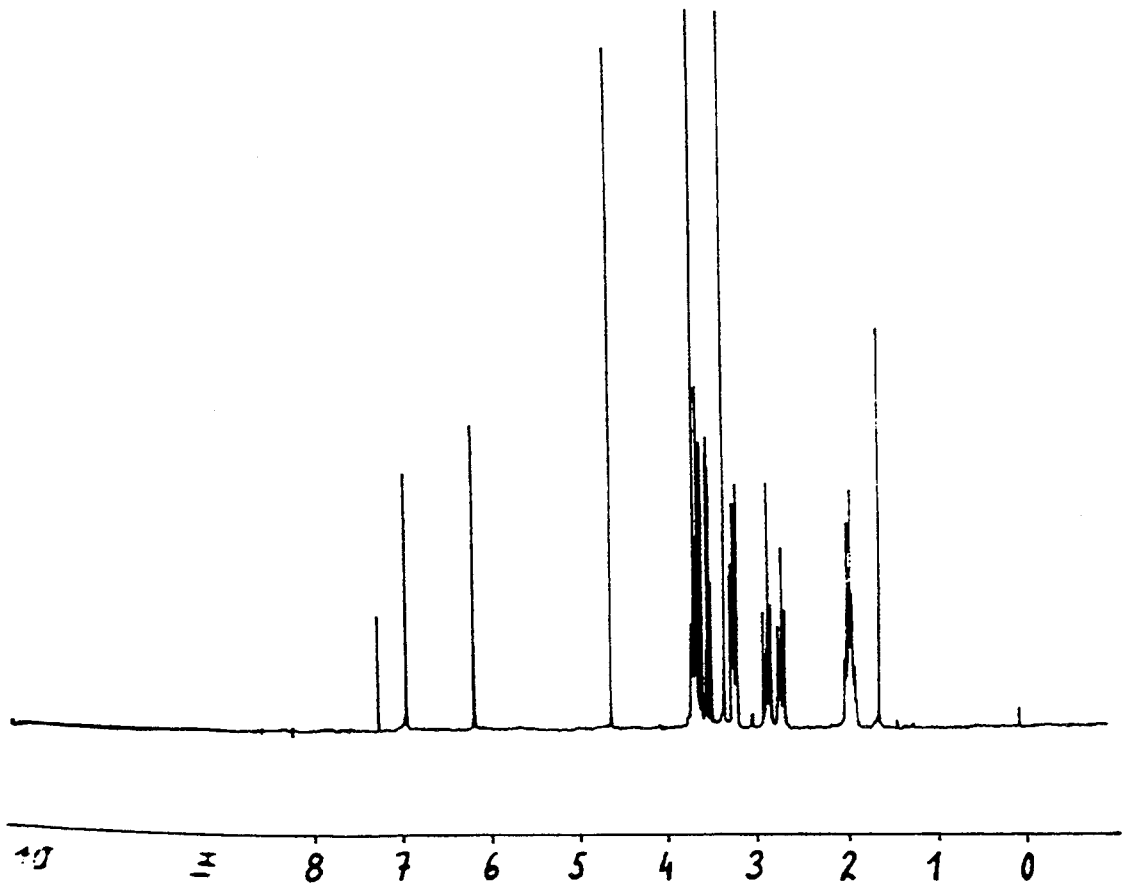
Figure 13:
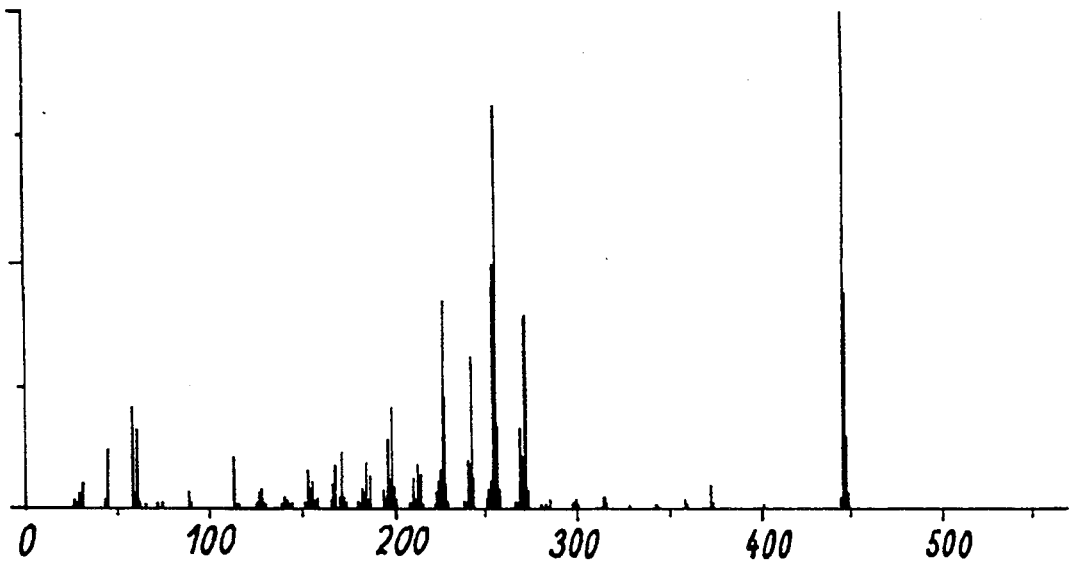

FIG. 12 shows the spectrum of the product, which confirms the expected structure.

EXAMPLE 7

Preparation of
2,3,6,7-tetrahydro-9-(9'-carboxyethyl-2',5',8'-trioxanonyl)-1H,5H,11H-(1)-benzopyrano-(6,7,8-ij)-quinolizinone-11 (compound 8) of formula

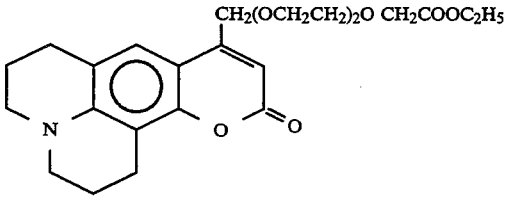

Into a 100 ml round-bottomed flask are introduced 2.23 g of 8-hydroxyjulolidine, 4.69 of compound 2, 13.5 ml of absolute ethanol and 1.85 g of zinc chloride. Heating takes place to boiling accompanied by stirring for 24 h and then the content of the flask is poured into a mixture of 450 ml of dichloromethane and 170 ml of water. The aqueous phase is extracted with twice 50 ml of dichloromethane and the organic phases are washed with 50 ml of water, followed by evaporation to dryness.

The crude product is purified on a silica column using as the eluent CH$_2$Cl$_2$ and then CH$_2$Cl$_2$:THF (95:5). This gives 5.25 g of compound 8, which corresponds to a 60% yield.

The product has the following characteristics.

1°) TLC (fluorescent silica K$_6$F CH$_2$Cl$_2$—THF (95:5) Rf=0.42, developed at 254 nm, 356 nm and with iodine.

2°) Mass spectrum (electron impact).

FIG. 3 shows the spectrum obtained and the molecular peak at M=445 confirms the mass of the product.

EXAMPLE 8

Preparation of 2,3,6,7-tetrahydro-9-(9′-carboxy-2′,5′,8′-trioxanonyl)-1H,5H,11H-(1)-benzopyrano-(6,7,8ij)-quinolizinone-11 (compound 9) of formula:

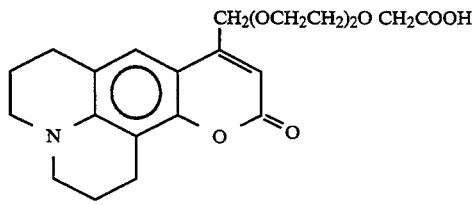

3.17 g (7.11 mmole) of compound 8 are dissolved in 63 ml of methanol and 95 ml of water containing 626 mg (15 mmole) of soda are introduced. Heating takes place to 50° C., accompanied by stirring for 1 h and protected from light and the temperature is then reduced to 20° C. Acidification takes place to a pH of 1.5 with 3N HCl, followed by stirring for 30 min. The pH is brought to 6.4 with 3N soda and stirring takes place for 30 min. The methanol is partly evaporated in the vacuo and the impurities are extracted with 200 ml of dichloromethane, followed by evaporation to dryness in vacuo and the taking up of the residue in 50 ml of ethanol. The mineral salts are filtered and made dry.

This gives 2.5 g of compound 9 in the form of an oil which slowly solidifies and which corresponds to an 84% yield.

The product has the following characteristics.

1°) TLC (fluorescent silica K$_6$F, butanol-acetic acid-water 60:20:20).

Rf-0.45, developed at 254 nm, 356 nm and with iodine.

2°) Mass spectrum (chemical ionization with ammonia).

Figure 14:
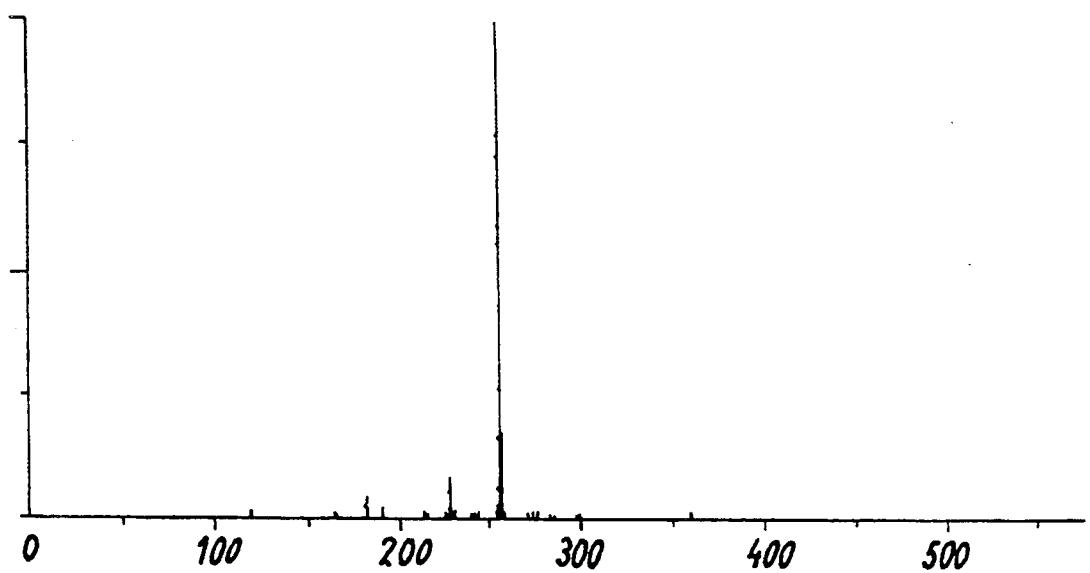

FIG. 14 shows the spectrum obtained and the peak at M=256 reveals a fragmentation between the carbon and the first oxygen of the side chain corresponding to the substituent R$^1$.

3°) NMR spectrum.

Figure 15:
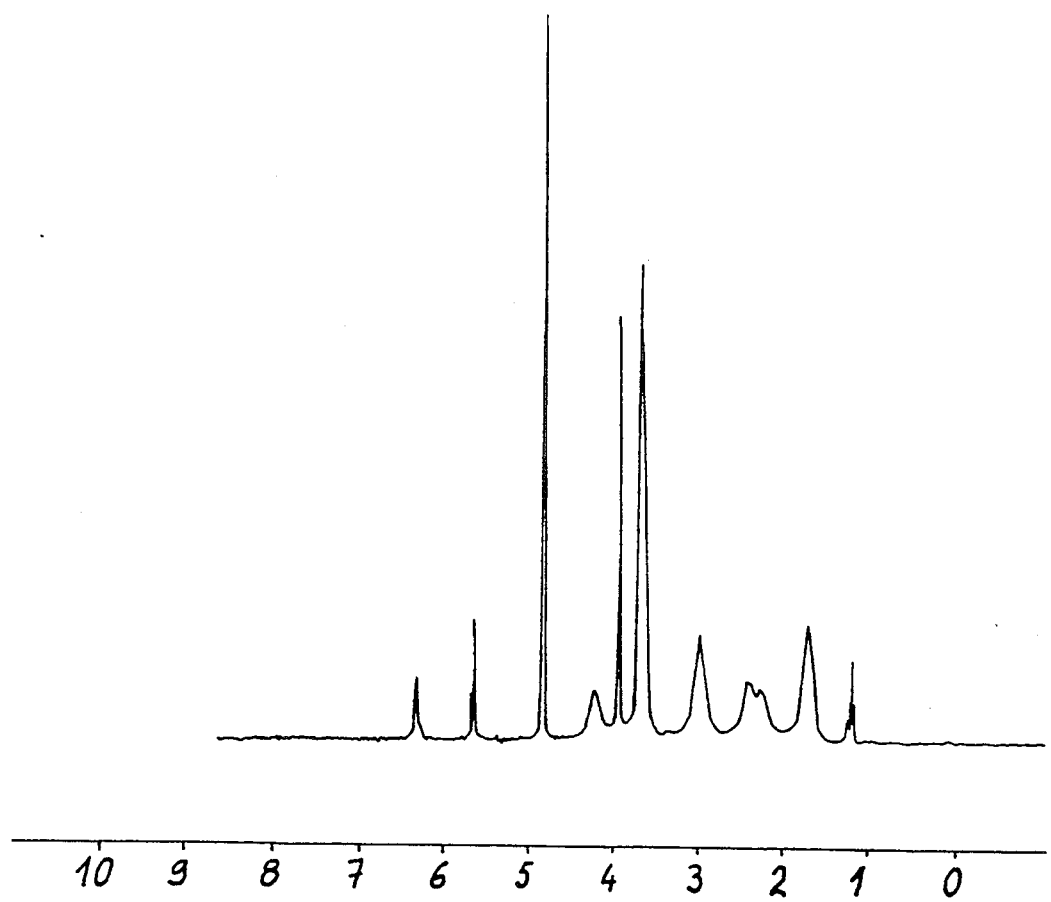

FIG. 15 shows the spectrum of the proton and confirms the structure of the compound.

Figure 16:
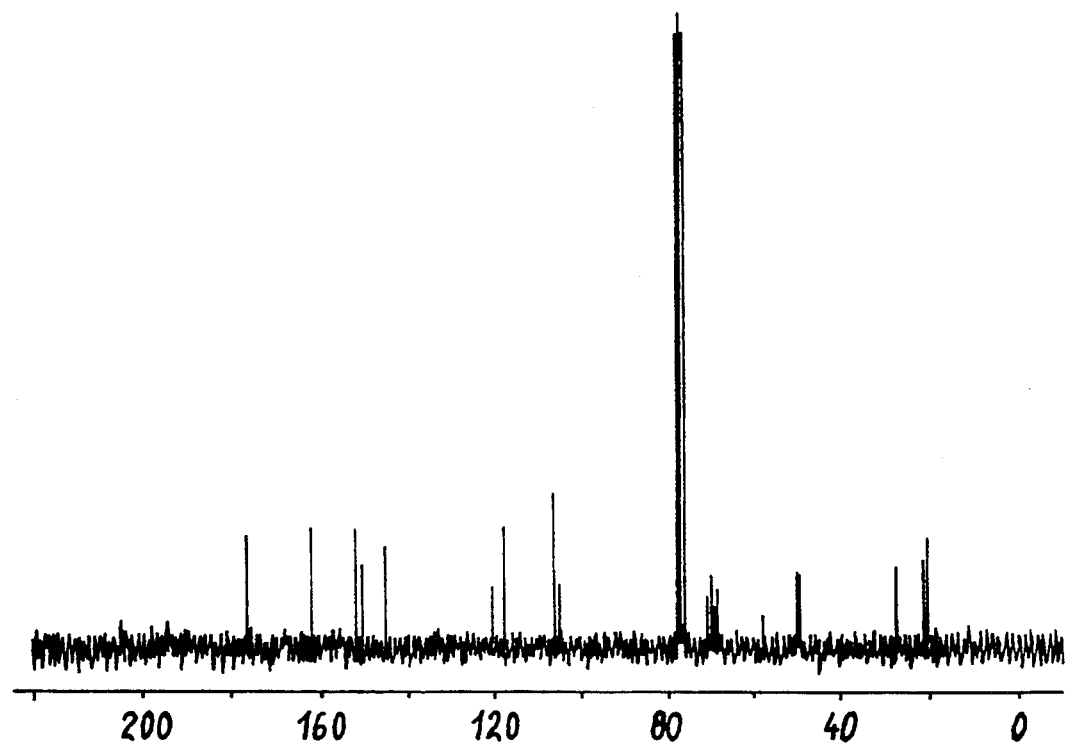

FIG. 16 shows the spectrum of carbon 13 of this compound.

EXAMPLE 9

Preparation of 7-hydroxy-4-(2′,5′,8′-trioxanonyl)coumarin (compound 10) of formula

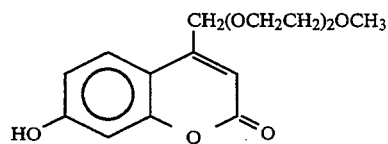

Into a 25 ml round-bottomed flask are introduced 3.3 g (0.03 mole) of resorcinol, 7.4 g (0.03 mole) of compound 1 and 7.5 ml of trifluoroacetic acid. Stirring takes place at 75° C. for 5 h and then the flask content is poured into a mixture of 300 g of water and ice. Extraction takes place with twice 150 ml of butanol and the butanolic phases are washed with twice 50 ml of water, followed by evaporation to dryness.

The crude product is purified by silica column chromatography using ethyl acetate as the eluent and the purest fractions are recrystallized in an ethanol-water mixture (30:70). This gives 2 g of compound 10, which corresponds to a 3% yield.

The product has the following characteristics.

1°) TLC (fluorescent silica K$_6$F, ethyl acetate).

Rf=0.48, developed at 254 nm, 356 nm and with iodine.

2°) Mass spectrum (chemical ionization with ammonia).

Figure 17:
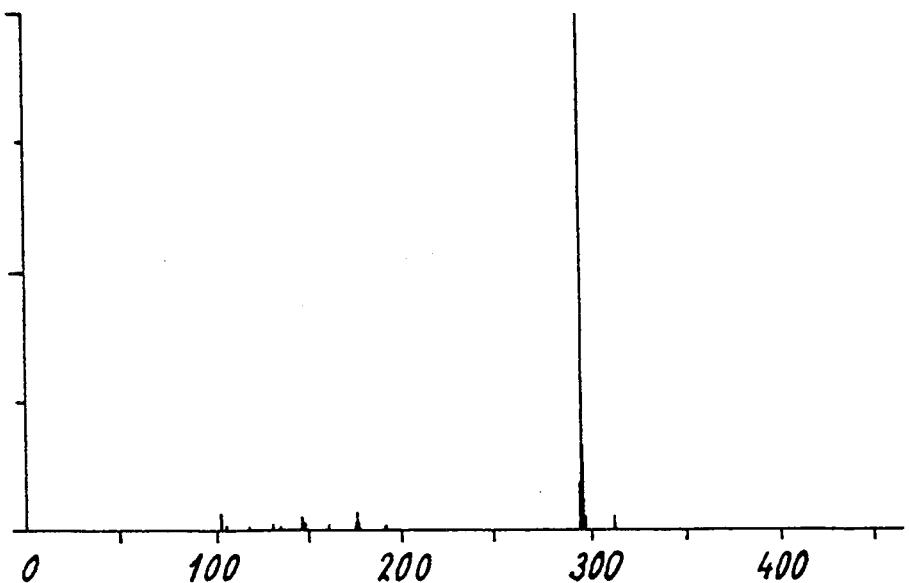

FIG. 17 shows the spectrum obtained and the peaks at 295 (M+1) and 312 (M+18) confirm the molecular mass of 294.

3°) NHR spectrum of the proton (200 MHz).

Figure 18:
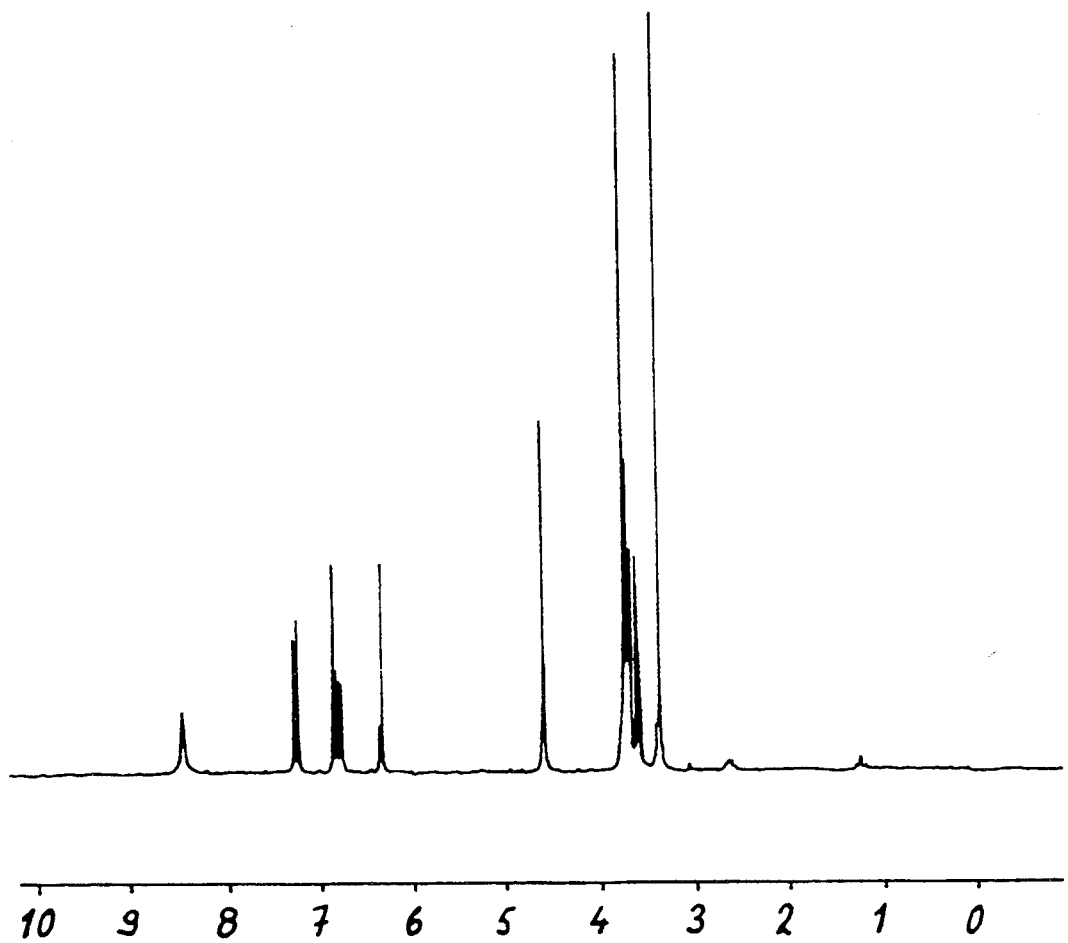

FIG. 18 shows the spectrum obtained and which confirms the structure of the compound.

4°) Solubility in water: 1 g/l.

5°) Solubility in the water-ethanol mixture (90:10): 7 g/l).

EXAMPLE 10

Preparation of 4-(2′,5′,8′-trioxanonyl)-esculetine (compound 11) of formula

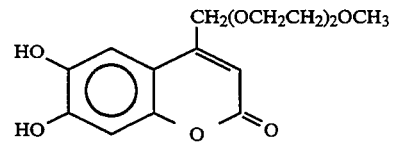

Into a 100 ml round-bottomed flask are introduced 3.05 g (12 mmole) of triacetoxybenzene, 3 g (12 mmole) of compound 1 and then 14 ml of sulphuric acid. Heating takes place to 80° C. for 30 min, followed by cooling and the pouring onto a mixture of 50 ml of water and 50 ml of n-butanol. The organic phase is separated and rinsed with 4 times 50 ml of water, followed by evaporation in vacuo.

The product is purified on the silica column using as the eluent a dichloromethane-methanol mixture (75:25). The purified fractions are evaporated, taken up in dichloromethane and then insolubles are eliminated and concentrated to dryness. This gives 270 mg of compound 11, which corresponds to an 8% yield.

The characteristics of the product are as follows:

1°) TLC (fluorescent silica K₆F, CH₂Cl₂—MeOH, 75:25).

Rf=0.85, developed at 254 nm, 356 nm and with ferric chloride.

2°) Mass spectrum (chemical ionization with ammonia).

Figure 19:
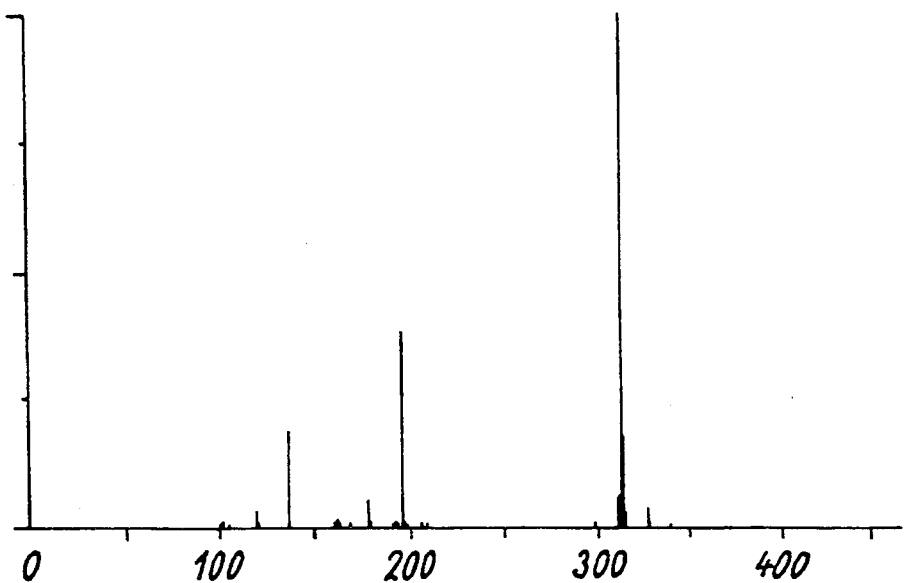

FIG. 19 shows the spectrum obtained and the peaks at 311 (310+1) and 328 (311+17) confirm the molecular mass of the product.

3°) NMR spectrum of the proton (200 MHz).

Figure 20:
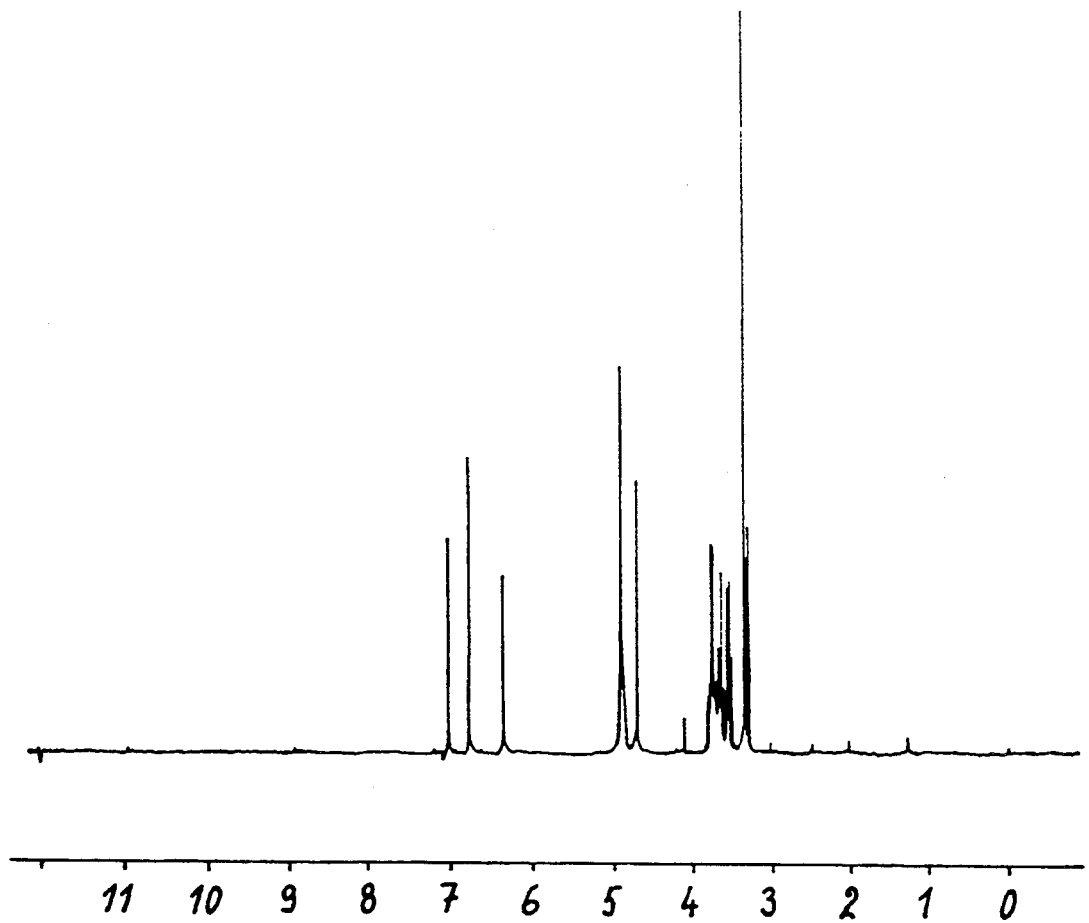

FIG. 20 shows the spectrum obtained, which confirms the structure of the compound.

EXAMPLE 11

Preparation of N-carbobenzyloxy-L-leucine-4-(2',5',8'-trioxanonyl)-7-coumarinylamide (compound 12) of formula

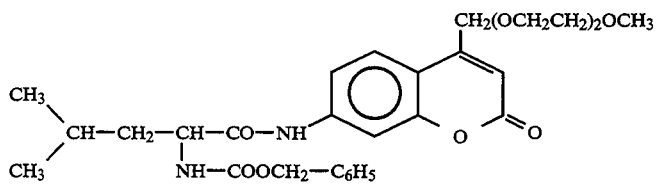

In this example, compound 4 is combined with N-carbobenzyloxy-L-leucine in order to prepare an enzyme substrate using dicyclohexyl carbodiimide (DCCI).

In a 25 ml Erlenmeyer flask dissolving takes place of 1.06 g (4 mmole) of N-carbobenzyloxy-L-leucine and 1.17 g (4 mmole) of compound 4 in 10 ml of dimethyl formamide. Accompanied by stirring introduction takes place of 989 mg (4.8 mmole) of DCCI, followed by stirring for 2 h and the filtration of the precipitate formed. Pouring occurs onto a mixture of 50 ml of water and 50 ml of dichloromethane, followed by the washing of the organic phase with 20 ml of 1N HCl, 20 ml of 0.5% sodium bicarbonate and 20 ml of water. The solution is then dried and concentrated to dryness. This gives 2 g of compound 12, which corresponds to a 92.6% yield.

The product has the following characteristics.

1°) TLC (fluorescent silica K₆F, butanol-acetic acid-water: 60:20:20).

Rf=0.72, developed at 254 and 356 nm.

2°) Mass spectrum (chemical ionization with ammonia).

Figure 21:
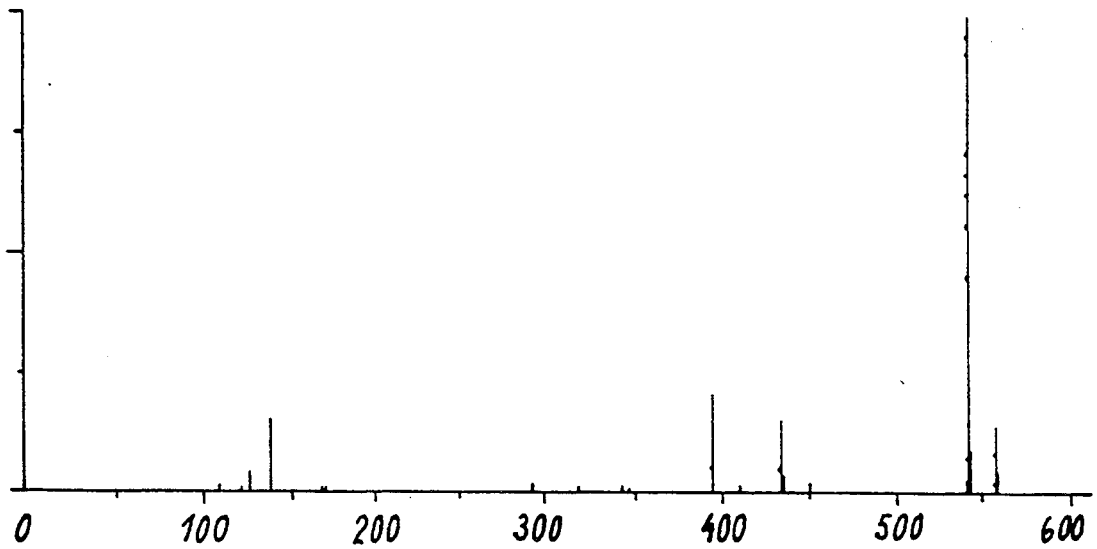

FIG. 21 shows the spectrum obtained and the peaks at 541 (M+1) and 558 (M+18) confirm the molecular mass of 540.

EXAMPLE 12

Preparation of N-carbobenzyloxy-L-leucine-4-(2',5',8'-trioxanonyl)-7-coumarinylamide (compound 12).

This example makes use of another process for preparing compound 12 of example 11. Use is made here of the coupling of compound 4 with N-carbobenzyloxy-L-leucine following the intermediate formation of a mixed anhydride of N-carbobenzyloxy-L-leucine.

Protected from moisture, introduction takes place into a 250 ml round-bottomed flask of 72 ml of anhydrous THF, 3.62 g (13.7 mmole) of N-carbobenzyloxy-L-leucine and 1.45 g (14.3 mmole) of N-methylmorpholine. Cooling takes place to −15° C., followed by the introduction of 1.96 g (14.3 mmole) of isobutyl chloroformate and reaction takes place for 5 min.

At this temperature, introduction takes place within 45 min of 4 g (13.7 mmole) of compound 4 dissolved in 144 ml of THF. This is followed by stirring for an additional 1 h at −15° C. and then at 20° C. until the next day. The insoluble product is filtered and evaporated to dryness. The residue is taken up with 50 ml of dichloromethane and washed with 20 ml of 1N HCl, 20 ml of 0.5% sodium bicarbonate and 20 ml of water, followed by drying and concentrating to dryness. This gives 17.8 g of compound 12, which corresponds to a 91.5% yield.

The product has the same characteristics as that of example 11.

EXAMPLE 13

Preparation of L-leucine-4-(2',5',8'-trioxanonyl)-7-coumarinylamide hydrochloride (compound 13) of formula

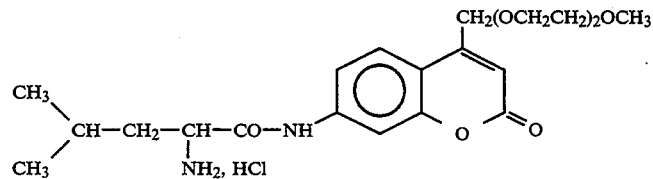

This compound is prepared from compound 12 by firstly eliminating the N-carbobenzyloxy group from the leucine by catalytic hydrogenation.

Into a hydrogenation flask are introduced 48 ml of ethanol, 8.5 g of compound 12 and 2.55 g of palladium on 5% charcoal. Purging takes place with nitrogen and the hydrogen is introduced with stirring for 5 h at atmospheric pressure and ambient temperature. The catalyst is filtered and evaporated to dryness. The product obtained is purified by silica column chromatography using THF as the eluent. This gives 2.7 g of compound 13, which corresponds to a 42% yield.

This is followed by the formation of the corresponding hydrochloride by dissolving 2.7 g of compound 13 in 5.5 ml of methanol and adding 730 µl of concentrated HCl. This is followed by evaporation to dryness in vacuo, the addition 6 ml of isopropanol and maintaining cold for 24 h. The precipitate formed is filtered, the product is again collected by diluting the filtrate with ethyl ether, so as to obtain in this way 2 g of hydrochloride of compound 13, which corresponds to a 68% yield.

The product has the following characteristics:

1°) TLC.
   a) fluorescent silica $K_6F$, butanol-acetic acid-water 60:20:20
      Rf=0.46, developed at 254 nm, 356 nm and with ninhydrin.
   b) fluorescent silica $K_6F$, THF
      Rf=0.25, developed at 254 nm, 356 nm and with ninhydrin.

2°) Mass spectrum (chemical ionization with ammonia).

Figure 22:
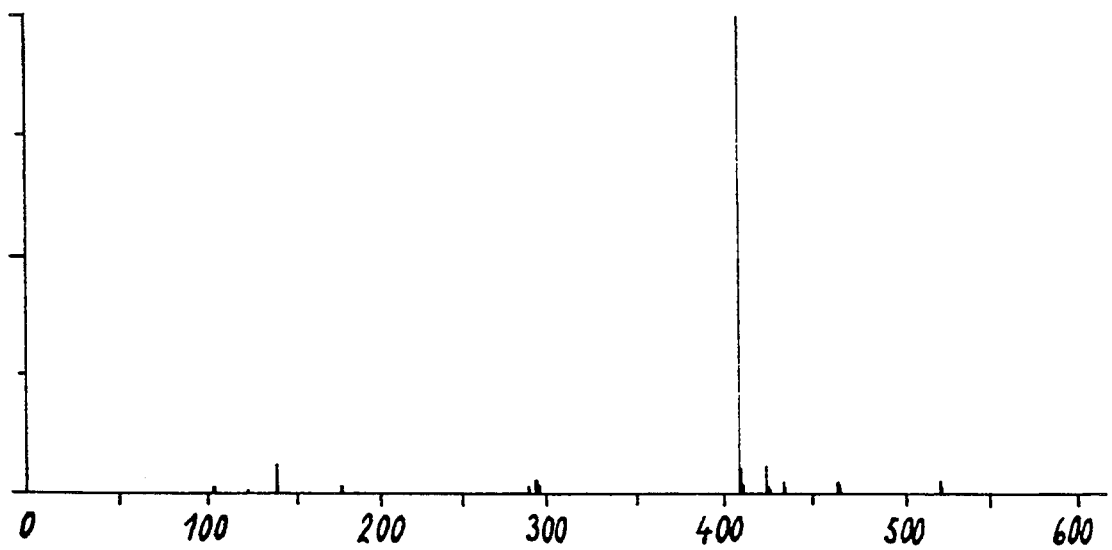

FIG. 22 shows the spectrum obtained and the peaks at 407 (M+1) and 424 (M+18) confirm the molecular mass of 406.

Figure 23:
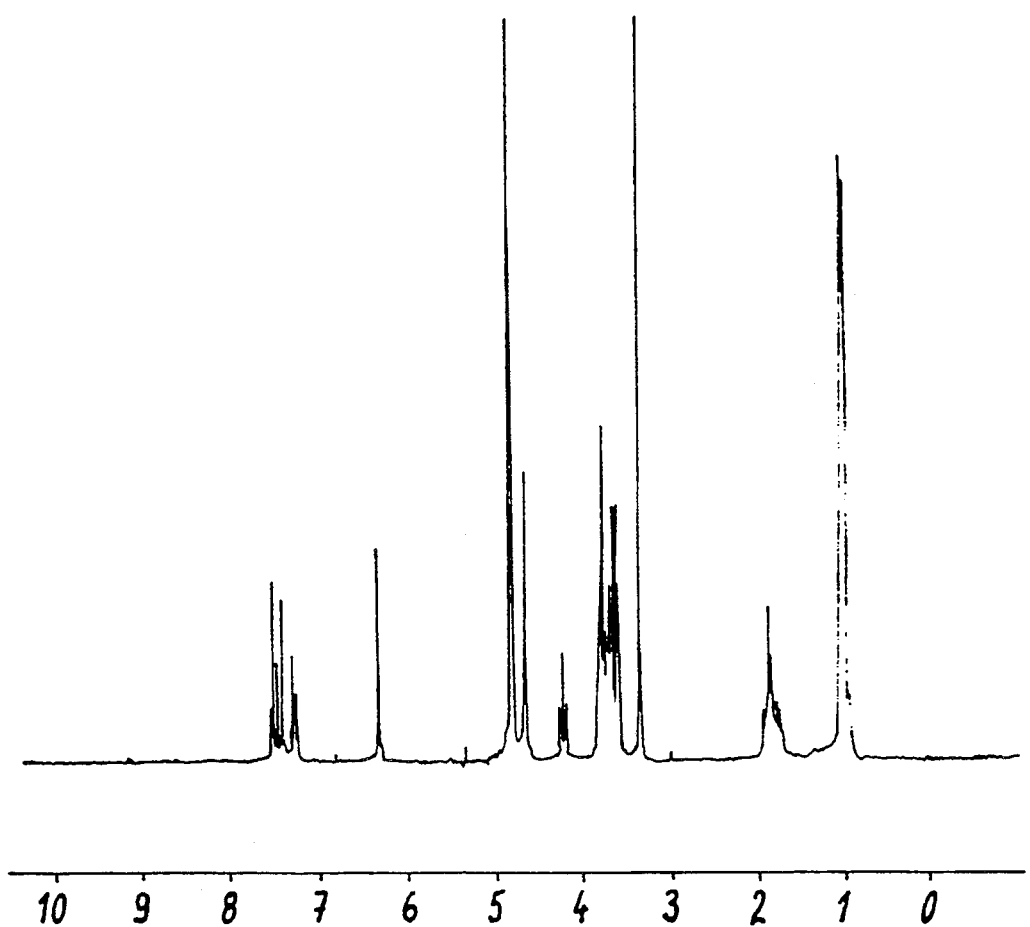

3°) NHR spectrum
FIG. 23 shows the spectrum of the proton, which confirms the structure of the product obtained.

EXAMPLE 14

This example studies the properties of compound 13 and its use as a hydrosoluble substrate of leucine aminopeptidase.

1. Studies of the enzymatic activity in the cell

As a result of the possible presence in the substrate Leu ATC (compound 13) of a trace of ATC, i.e. 7-amino-4-(2',5',8'-trioxanonyl)-coumarin, which is the hydrolysis product, use was made of a kinetic method for determining the enzymatic activity of leucine aminopeptidase, i.e. the signal is constituted by the fluorescence intensity difference at 2 minutes and 12 minutes. In this way it is possible to eliminate the interference of the ATC present prior to hydrolysis.

a) Determination of the optimum wavelength

The excitation and emission spectra of ATC and leucine-ATC (compound 13) were plotted on the basis of $10^{-7}M$ solutions in the Tris buffer at pH 7.8.

The maxima obtained are given in table 1 with the corresponding maxima of commercial substrates derived from 7-amino-4-methyl-coumarin (Leu-AMC) or 7-amino-4-coumarinyl-methane sulphonic acid (GlyGly Arg AMCS).

TABLE 1

Maximum excitation/fluorescence and measurement wavelengths (in nm) for derivatives of ATC, AMC and AMCS.

| | Substrate (nm) | Hydrolysis product (nm) | Measurement (nm) |
|---|---|---|---|
| Compound 13 | | | |
| (Leu ATC) | 330/405 | 350/465 | 370/480 |
| Leu AMC | 327/390 | 345/440 | 380/440 |
| GlyGly Arg AMCS | 336/409 | 362/462 | 380/462 |

The position of the excitation and fluorescence spectra of compound 13 (Leu-ATC) and the corresponding hydrolysis product (ATC) is intermediate between those of the AMC and AMCS derivatives, whilst its Stokes displacement is greater.

At the wavelength used for the measurement, the ratio of the fluorescence intensities of the hydrolysis product and the substrate at equimolar concentration is approximately 400 for ATC, 300 for AMC and 250 for AMCS. Thus, the fluorescence of the substrate does not interfere with that of the hydrolysis product.

b) Determination of the characteristics of the enzymatic reaction

The initial speed of the reaction was studied for a concentration of the substrate constituted by compound 13 (Leu-ATC) between $2 \times 10^{-5}$ mole/l and $2 \times 3^{-3}$ mole/l using the following reagents:

Crystalline Leu-ATC hydrochloride of example 13: aqueous solutions $4 \times 10^{-5}$ to $4 \times 10^{-3}$ mole/l, Leucine aminopeptidase (Sigma, ref N5006): aqueous solution at 7.53 μg/ml in 0.2M Tris buffer, pH7.8, Tris buffer: solution A: 0.2M Tris, i.e. 24.23 g/l, solution B: 0.1M HCl.

This buffer is prepared by mixing 25 ml of solution A and 33.7 ml of solution B and by topping up to 100 ml with water. The pH must be 7.8.

1.17N perchloric acid solution (1/10 dilution of the pure acid).

For this determination, preparation firstly takes place in tubes of the following range of substrate concentrations (compound 13, Leu-ATC): 0-2-4-10-20-50-10-0-200 $\times 10^{-5}M$ (final concentration).

To each tube is added a concentration of 1.51 μg/ml of Leucine aminopeptidase, everything being dissolved in the Tris buffer at pH 7.8, preheated to 37° C., whilst the tubes are in a water bath thermostatically controlled to 37° C. After 2 min, 250 μl are removed from each tube and poured into tubes containing 250 μl of perchloric solution and 750 μl of water. The same operation is repeated after 6 min. All the tubes are diluted to 1/1000. The intensity of the fluorescence IF is measured at 370/480 nm. The difference of the intensities at 6 and 2 min: IF(6)-IF(1) constitutes the signal.

The corresponding ATC concentration is calculated relative to a calibration range between $10^{-9}$ and $10^{-8}M$. The results are given in the following table 2:

TABLE 2

| Leu—ATC concentration | | | | | | | | |
|---|---|---|---|---|---|---|---|---|
| (in $10^{-5}$ M) | 0 | 2 | 4 | 10 | 20 | 50 | 100 | 200 |
| IF(6)-IF(2) | 0 | 5.5 | 11.5 | 21 | 38.5 | 45 | 47 | 48 |
| ATC concentration in working solution (in nM) | 0 | 1.38 | 2.88 | 5.25 | 9.63 | 11.25 | 11.75 | 12.0 |
| ATC concentration in hydrolysis solution (in μM/min) | 0 | 1.7 | 3.6 | 6.6 | 12.0 | 14.1 | 14.7 | 15.0 |

The speed constant kcat is calculated by the ratio Vm/Ez, in which Vm is the maximum speed in μmole/s/mg/Ez and Ez is the enzyme quantity in 1 mg, expressed in μmole. The molar mass of Leucine aminopeptidase is 300000.

Figure 24:
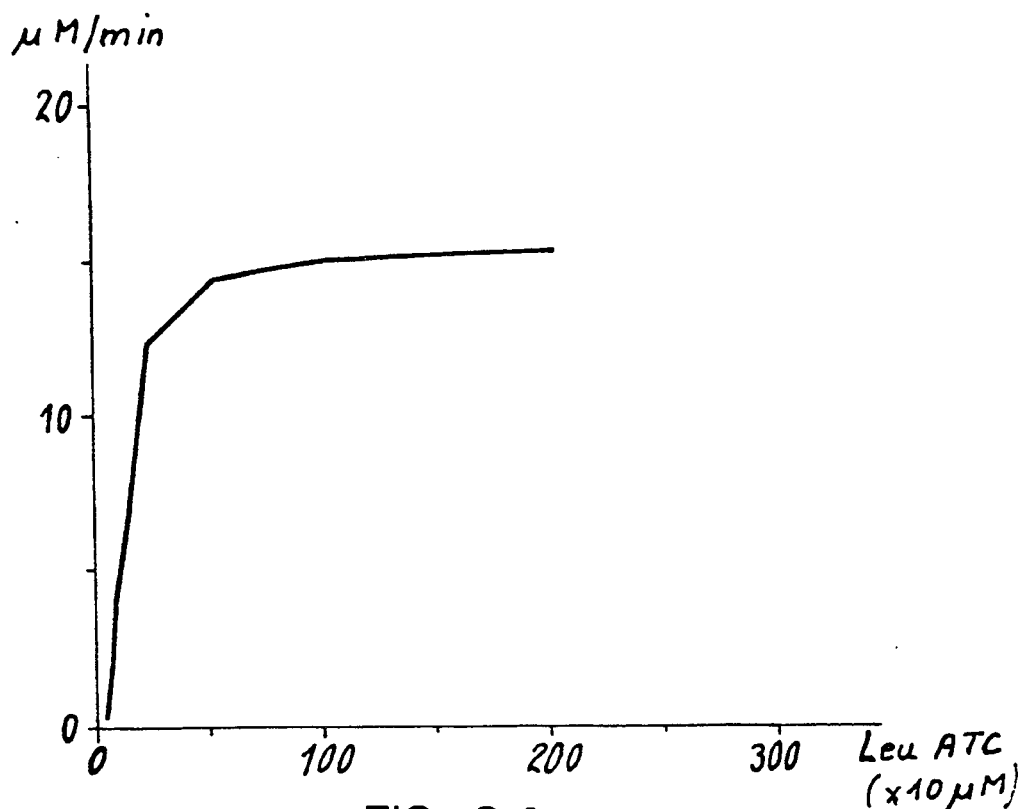
FIG. 24. A curve representing the initial speed (in μM/min) of the enzymatic reaction in the case of an enzymatic substrate according to the invention, as a function of the substrate concentration (in μM).

FIG. 24 is a curve illustrating the evolution of the initial speed (in μm/min) as a function of the substrate concentration (Leu-ATC) expressed in μm.

This curve has a hyperbolic behaviour characteristic of a Michaelis kinetics. The experimental points were adjusted to the corresponding equation by non-linear regression (Graphpad software) and made it possible to determine the affinity constant Km, the maximum speed Vm and the speed constant kcat (ratio of the maximum speed to the enzyme concentration). The results, compared with those of known substrates, are given in table 3.

TABLE 3

|  | Km (mM) | Vm (μmole/mg Ez/min) | kcat (s$^{-1}$) |
| --- | --- | --- | --- |
| Compound 13 | | | |
| Leu ATC | 0.11 | 10.3 | 51.5 |
| Leu AMC | 0.16 | 4.0 | |
| Leu-βnaphthylamide | 0.15 | 5.5 | |

The affinity of Leu-ATC for Leucine aminopeptidase is better than that of the two other substrates, whilst the maximum speed is higher. This may be due to the fact that the reaction medium contains no organic solvent, unlike in the case of the other substrates. In addition, the comparison of Leu-ATC and Leu-AMC reveals that the presence of the hydrosoluble side chain R$^1$ is not prejudicial to the enzymatic reaction, which is an advantage compared with substrates derived from 7-amino-4-coumarinyl-methane-sulphonic acid, in which the hydrosoluble sulphonic group greatly decreases the maximum speed and affinity.

c) Determination of the analytical characteristics of the reaction

The reaction conditions were determined following the preceding stage. The Leu-ATC substrate concentration was chosen to give a maximum speed (1 mM). The reaction time was made 12 minutes by measuring the difference of the fluorescence intensities at 12 and 2 minutes. In order to evaluate the quantification limit, measure the repeatability and test the linearity, 6 g of enzymes were prepared containing concentrations of 0–0.05–0.10–0.25–0.50–1 μg/ml using the same reagents as previously and giving the following range:

| Ez (mg/ml) | 0 | 0.05 | 0.10 | 0.25 | 0.50 | 1 |
| --- | --- | --- | --- | --- | --- | --- |
| Leu—ATC (4 × 10$^{-3}$ M) | 250 | 250 | 250 | 250 | 250 | 250 |
| Tris buffer | 750 | 740 | 730 | 700 | 650 | 550 |
| Enzyme 5 μg/ml | 0 | 10 | 20 | 50 | 100 | 200 |

In order to carry out the evaluation, a series of tubes was prepared containing 750 μl of water+250 μl of 1.17N perchloric solution and at time 2 min, transfer thereto took place of 250 μl of each sample of the enzyme range. The same took place at time 12 min. This was followed by the dilution of all the tubes to 1/200 in water and the reading of the fluorescence (370/480 nm) with a gain of 2 on the Perkin Elmer LS3B fluorimeter.

Figure 25:
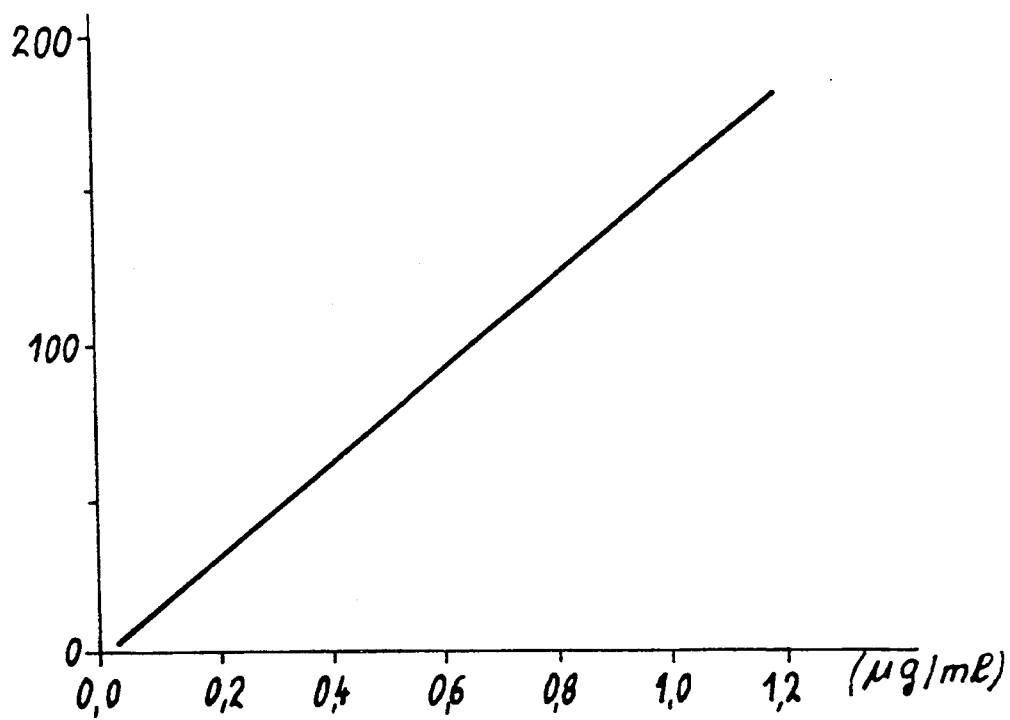
FIG. 25. A calibration curve showing the fluorescence intensity as a function of the enzyme concentration (μg/ml).

The results obtained are given in FIG. 25, with which is the mean calibration curve illustrating the variation of the fluorescence intensity as a function of the enzyme concentration (μg/ml). This calibration curve was determined by linear regression. The mean standard deviation is 153±7.36 for the gradient and −3.10±1.16 for the intercept.

The linearity test is significant at the 5% threshold (F=0.554).

The quantification limit, calculated by the ratio −3 b/a, is 0.02 μg/ml.

The repeatability, evaluated by the variation coefficient, is 17% at 0.05 μg/ml, 8% at 0.25 μg/ml and 4% at 1 μg/ml.

Therefore the detection limit is more favourable than that obtained with Leu-AMC, which is 0.03 μg/ml.

EXAMPLE 15

Preparation of N-carbobenzyloxy-L-arginyl-4-(2′,5′,8′-trioxanonyl)-7-coumarinylamide hydrochloride (compound 14 of formula

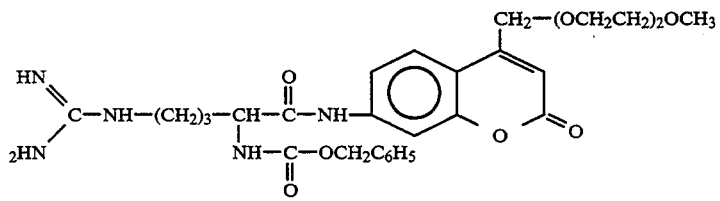

In this example compound 4 is combined with N-carbobenzyloxy-L-arginine using dicyclohexyl carbodiimide (DCCI) as the combining or coupling agent.

In a 100 ml round-bottomed flask are dissolved 3.45 g (10 mmole) of N-carbobenzyloxy-arginine hydrochloride and 1.467 g (5 mmole) of compound 4 in 15 ml of dimethylformamide. Accompanied by stirring introduction takes place of 1.05 g (5 mmole) of DCCI, accompanied by stirring for 20 h. This is followed by filtering and the elimination of the precipitate.

The solvent is evaporated in vacuo and taken up by a mixture of 25 ml of ethyl acetate and 2.5 ml of methanol. The oil which separates is taken up by a mixture of 1.5 ml of DMF and 5 ml of methanol, to which is slowly added 60 ml of ethyl acetate. The gummy precipitate formed solidifies in the vacuum desiccator: 2.14 g.

The crude product obtained is purified on a silica column using as eluents ternary mixtures of dichloromethane, methanol and acetic acid 85:15:5 and then 85:20:5.

On the 34 10 ml fractions collected, fractions 19 to 30 are concentrated. The concentrate, taken up twice in ethanol and re-evaporated, is subject to ether addition and stirred. The product is filtered and dried in vacuo giving a 19.5% yield of 605 mg.

The product has the following characteristics:
1°) TLC

Fluorescent silica K$_6$F; eluting solvent: dichloromethane/methanol/acetic acid 85:20:5-developing at 254 and 356 nm (blue violet spot); Rf 0.63.

2°) NMR spectrum.

Figure 26:
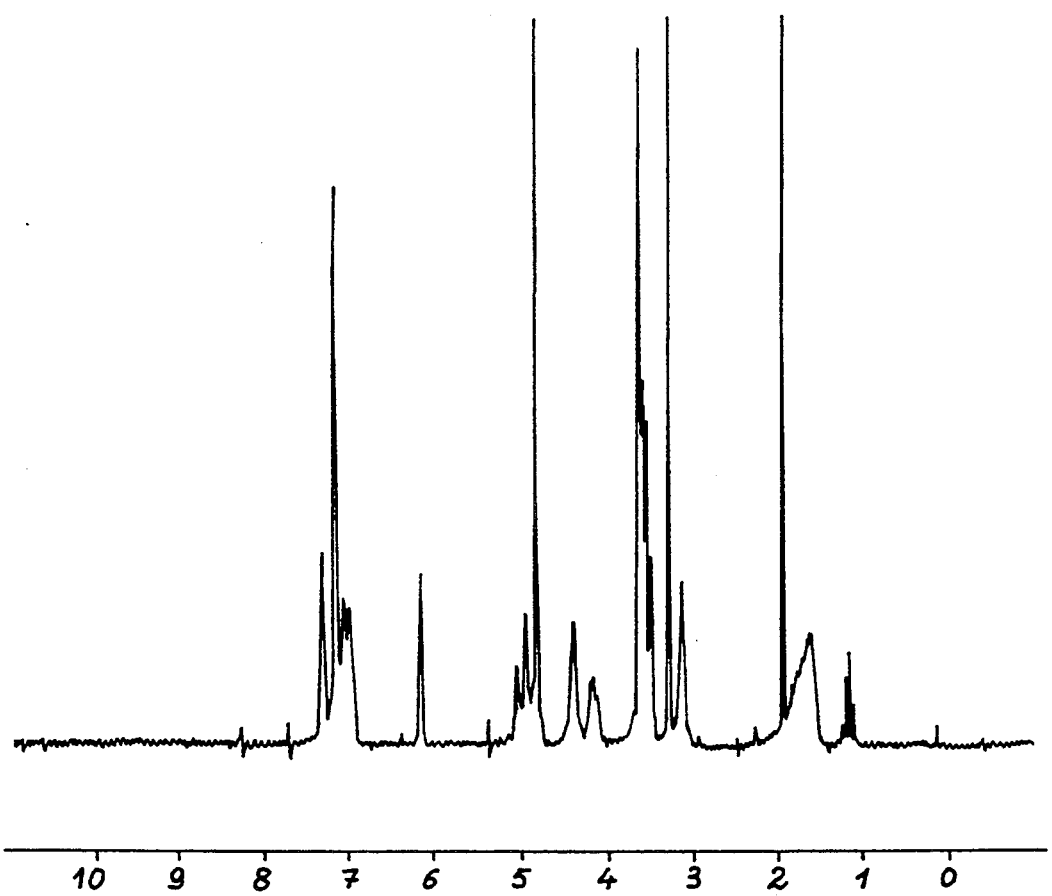

FIG. 26 shows the spectrum of the proton confirming the structure of the product obtained and showing a solvation with an acetic acid molecule.

3°) Mass spectrum (chemical ionization with ammonia).

Figure 27:
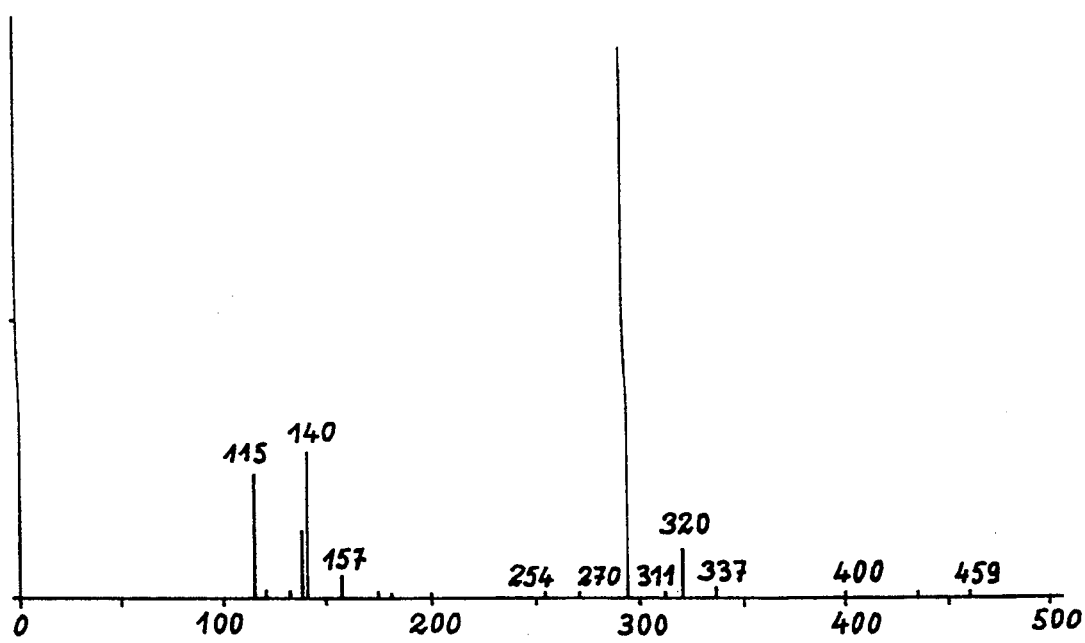

FIG. 27 shows the spectrum obtained. The molecule is highly fragmented and the main peak at 294 (293+1) representing the molecule of compound 4 is the most stable part.

EXAMPLE 16

This example studies the hydrolysis of Z-Arg-ATC (compound 14) by trypsin.

1°) Determination of the optimum wavelength.

Figure 29:
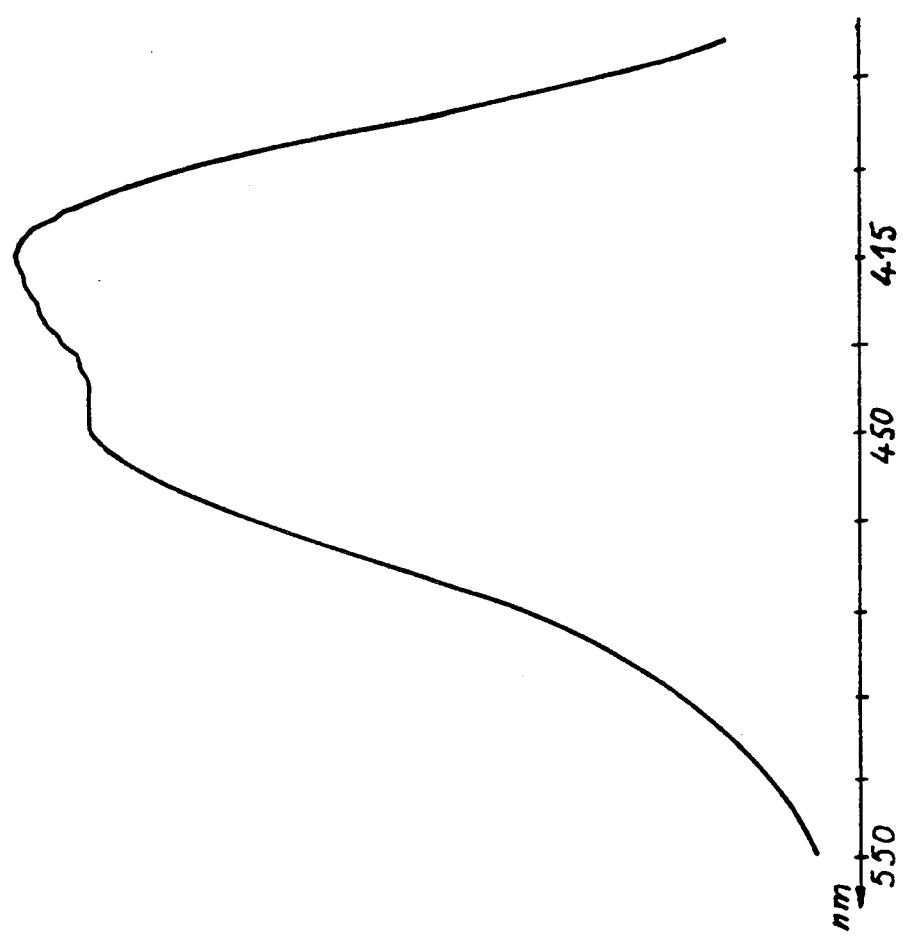
FIG. 29. The emission spectrum of a compound according to the invention.
Figure 28:
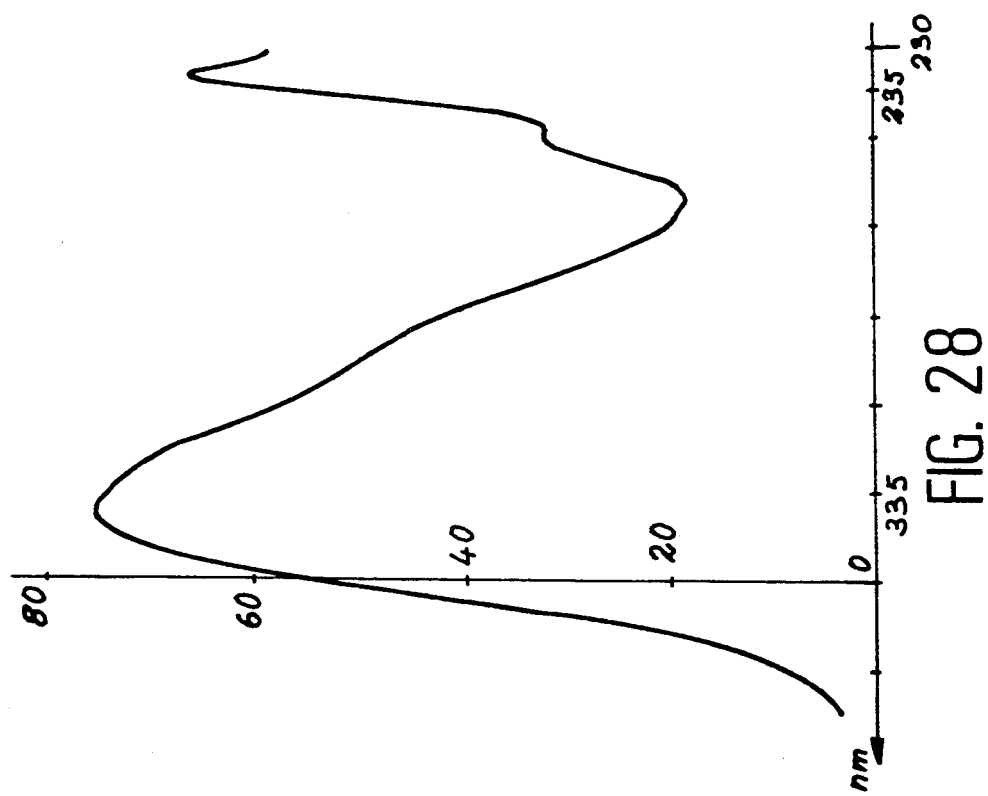
FIG. 28. The excitation spectrum of a compound according to the invention.

The excitation and emission spectra of ATC and Z-Arg-ATC were plotted on the basis of $10^{-7}$M solutions in the 50 mM Tris buffer at pH 8 containing 10 mM of $CaCl_2$. The excitation and emission spectra of Z-Arg-ATC are respectively shown in FIGS. 28 and 29. The maxima obtained are indicated in table 4 with the corresponding maxima of Leu-ATC.

TABLE 4

Wavelengths (in nm) of the excitation/fluorescence and measurement maxima for ATC derivatives.

| | Substrate (nm) | Product (nm) | Measurement (nm) |
|---|---|---|---|
| Leu—ATC | 330/405 | 350/465 | 370/480 |
| Z—Arg—ATC | 355/415 and 450 | 350/465 | 380/490 |

The presence of Arg in place of Leu on the amine of the ATC leads to a slight displacement of the spectra towards the red (bathochromic effect), which imposes a change to the measurement wavelengths in the same direction, in order to avoid interference of the substrate in the fluorescence of the product.

2°) Characteristics of the enzymatic reaction.

a) Reagents

Crystalline Z-Arg-ATC hydrochloride (Seratec): $10^{-3}$M solution in Tris buffer, pH 8.0+$CACl_2$, 10 mM.

Pig pancreas trypsin (SIGMA T0134): $10^{-3}$M solution in Tris buffer, pH 8.0+$CACl_2$, 10 mM.

Tris buffer: solution A: 0.2M Tris, i.e. 24.23 g/l+$CaCl_2$, 40 mM, i.e. 5.88 g/l; solution B: 0.1M HCl.

This buffer is prepared by mixing 250 ml of solution A with 268 ml of solution B and by topping up to 1 liter with water.

Acetate buffer: solution A: 0.02M acetic acid; solution B: 0.02M sodium acetate.

This buffer is prepared by mixing volume by volume solutions A and B to obtain a buffer at pH 4.75.

Aqueous 1.17N perchloric acid solution (1/10 dilution of pure acid).

b) Procedure

The following substrate concentration range was prepared in tubes: 0–0.2–0.5–1–2–5–10×$10^{-4}$M (final concentration).

To each tube was added a concentration of 6.67 μg/ml of trypsin, everything being dissolved in the Tris buffer pH 8.0+$CaCl_2$, 10 mM and at ambient temperature. The enzyme is added at time 0. After 2 minutes, 250 μl are removed from each tube and poured into tubes containing 250 μl of 1.17N perchloric acid and 500 μl of water. The tubes are centrifuged and then the solution is diluted to 1/250 in the acetate buffer. The same operation is repeated at 17 min. The fluorescence intensity is measured at 380/490nm. The difference of the intensities at 17 and 2 min constitutes the signal.

The corresponding ATC concentration is calculated compared with a calibration range from $5\times10^{-9}$ to $2\times10^{-7}$M.

The results are given in the following table 5.

TABLE 5

| |Arg—ATC| × $10^{-4}$ M | 0 | 0.2 | 0.5 | 1 | 2 | 5 | 10 |
|---|---|---|---|---|---|---|---|---|
| IF(17)–IF(2) | 0 | 3.7 | 7.7 | 16.9 | 29.8 | 38.9 | 42.4 |
| |ATC|nM working solution | 0 | 3.36 | 7.00 | 15.4 | 27.1 | 35.4 | 38.6 |
| |ATC| μM/min | 0 | 0.224 | 0.467 | 1.03 | 1.81 | 2.36 | 2.57 |

TABLE 5-continued hydrolysis soluion

This was followed by the determination of Km, Vm, kcat and the ratio kcat/Km. The results obtained are given in table 6, which also gives for comparison purposes the values obtained with Z-L-Arg-AMC and $B_z$ DL Arg-AMC and $B_z$-L-Arg-AMC.

TABLE 6

| | Km (mM) | Vm (nmole/min/mg Ez) | kcat ($s^{-1}$) | kcat/Km $M^{-1}s^{-1}$ |
|---|---|---|---|---|
| Z—L—Arg—ATC | 0.195 | 474 | 0.19 | 975 |
| Bz—L—Arg—AMC | 0.11 | — | 0.42 | 3800 |
| Z—L—Arg—AMC | 0.20 | — | 0.89 | 4500 |
| Bz—DL—Arg—AMC | 0.25 | — | 0.20 | 800 |

Thus, Km is 0.195 mM and Vm is 3.16 μM/min.

The maximum speed is 474 nmole/min/mgEz, corresponding to kcat=$0.19s^{-1}$ and a kcat/Km ratio of $975M^{-1}s^{-1}$.

Therefore the substrate Z-L-Arg ATC is comparable with Bz-DL-Arg-AMC from the standpoint of its affinity and activity. However, the maximum speed is approximately 4 to 5 times below that of Z-L-Arg AMC. This difference is not considerable and can be compensated by a slightly longer measurement time.

3°) Analytical characteristics.

Six calibration ranges containing a final enzyme concentration of 0–0.42–0.84–1.67–3.33–6.67 μg/ml were prepared. Each calibration curve was determined by linear regression. The mean standard deviation is $2.45\times10^{-3}\pm0.003\times10^{-3}$ for the gradient and $4.80\times10^{-3}\pm2.53\times10^{-3}$ for the intercept The linearity test is significant at the 5% threshold (W=0.245). The quantification limit, calculated by the ratio $3\sigma_b/a$ is 0.05 μg/ml. The repeatability, evaluated by the variation coefficient, is 9.4% at 0.42 μg/ml, 5.9% at 0.84 μg/ml and 1.3% at 6.67 μg/ml. The detection limit for trypsin by Z-L-Arg ATC is therefore of the same order of magnitude as that obtained with substrates derived from AMC.

EXAMPLE 17

Preparation of N-carbobenzyloxy pyroglutamyl-4-(2',5',8'-trioxanonyl)-7-coumarinylamide (compound 15)

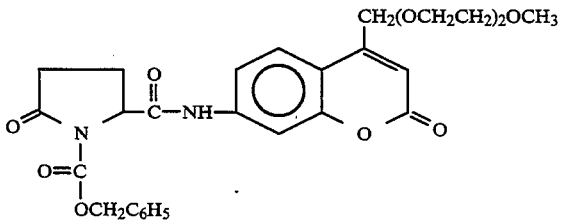

In this example, compound 4 is coupled with N-carbobenzyloxy pyroglutamic acid by using dicyclohexyl carbodiimide (DCCI) as the coupling agent.

In a 100 ml round-bottomed flask are dissolved 2.24 g (8.5 mmole) of N-carbobenzyloxy pyroglutamic acid and 2.5 g of compound 4 (8.5 mmole) in 30 ml of dimethyl formamide. Accompanied by stirring, introduction takes place of 1.76 g (8.5 mmole) of DCCI and stirring takes place for 20 h. This is followed by filtration and the elimination of the precipitate.

The filtrate is poured onto a mixture of 150 ml of water and 150 ml of dichloromethane. The organic phase is washed with 4×100 ml of 1N hydrochloric acid, 100 ml of water, 100 ml of 5% bicarbonate and 50 ml water.

The organic phase is dried on magnesium sulphate and evaporated in vacuo. The residue is crystallized in 20 ml of ethyl acetate giving a yield of 2.5 g (56%).

The product has the following characteristics.

1°) TLC fluorescent silica K$_6$F; eluting solvent: ethanol/cyclohexane/THF 30:70:5. Development at 254 and 356 nm (blue violet spot), Rf=0.16.

Figure 30:
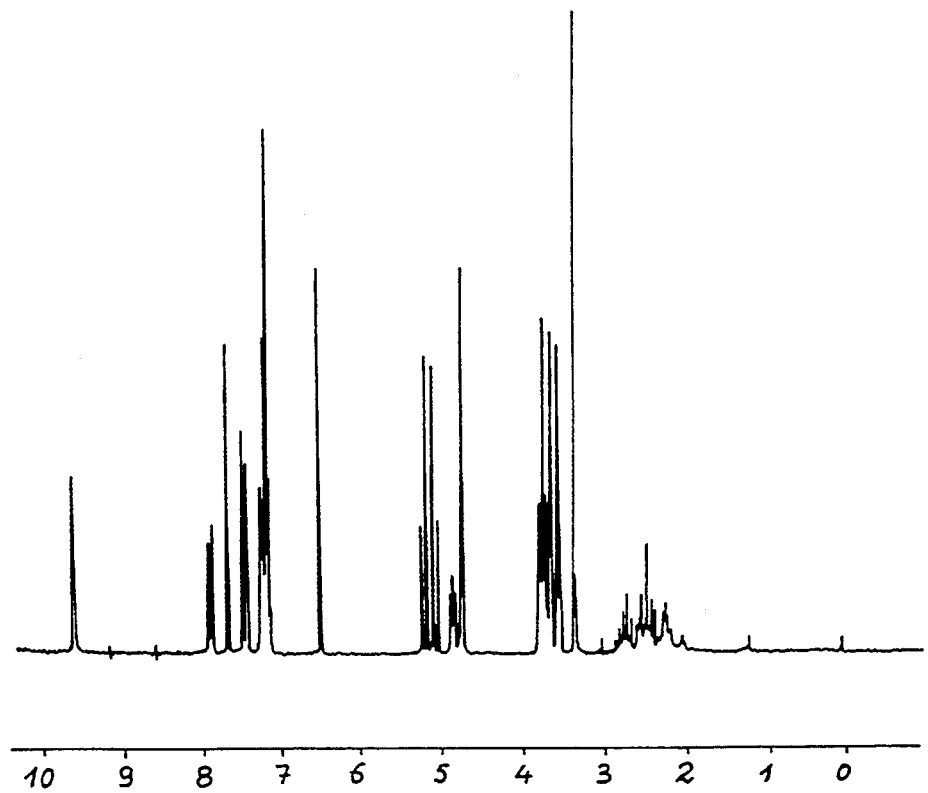

2°) NMR spectrum:

FIG. 30 gives the spectrum of the proton confirming structure of the product obtained.

3°) Mass spectrum: (chemical ionization with ammonia).

Figure 31:
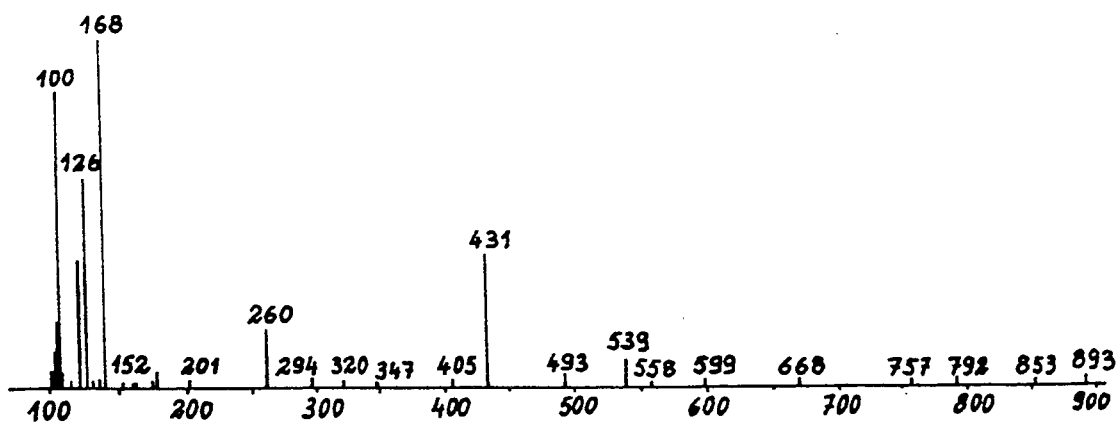

FIG. 31 shows the spectrum obtained. The peak at 539 represents the molecular peak at +17.

EXAMPLE 18

Preparation of pyroglutamyl-4-(2',5',8'-trioxanonyl)-7-coumarinylamide (compound 16)

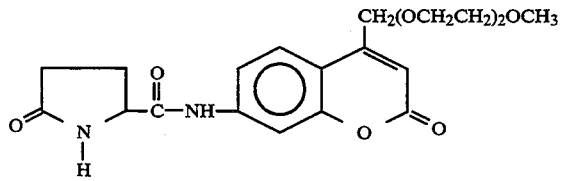

In this example, compound 15 is hydrogenated dissolved in tetrahydrofuran.

Into a hydrogenation flask are introduced 70 ml of tetrahydrofuran, 2.4 g of compound 15 and 360 mg of palladium on 10% charcoal. Purging takes place with nitrogen and hydrogen is introduced. Stirring takes place for 5 h at atmospheric pressure and ambient temperature. After filtering the catalyst evaporation takes place to dryness and recrystallization occurs in 40 ml of ethyl acetate giving a yield of 1.32 g (74.5%).

The product has the following characteristics.

1°) TLC

Fluorescent silica K$_6$F: eluting solvent dichloromethane/methanol 90:10; development at 254 and 356 nm (blue violet spot)-Rf=0.39.

2°) Mass spectrum (chemical ionization with ammonia).

Figure 32:
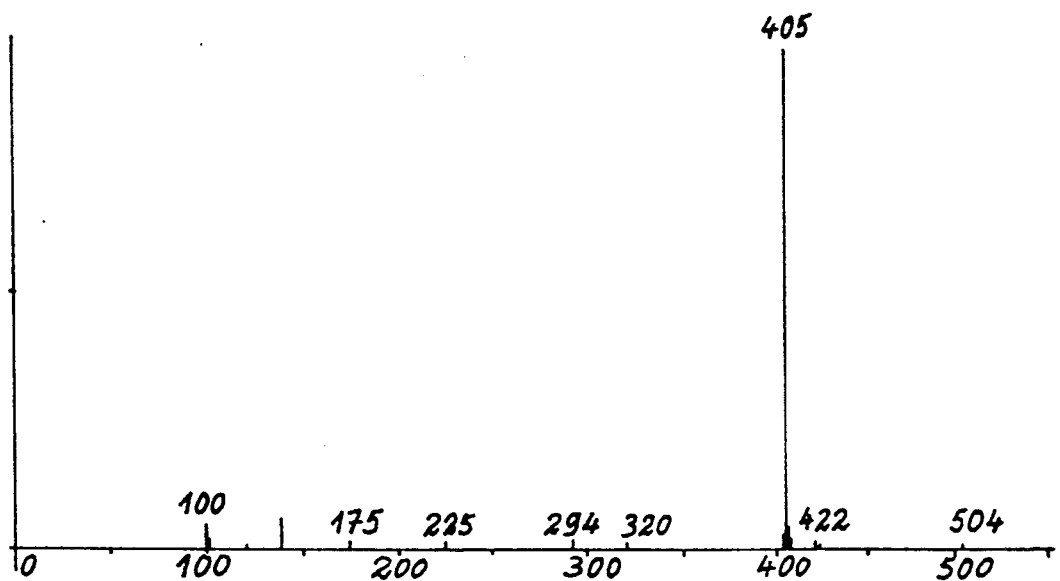

FIG. 32 shows the spectrum obtained. The peak at 405 represents the molecular peak and that of 422 the +17 molecular peak.

3°) NHR spectrum

Figure 33:
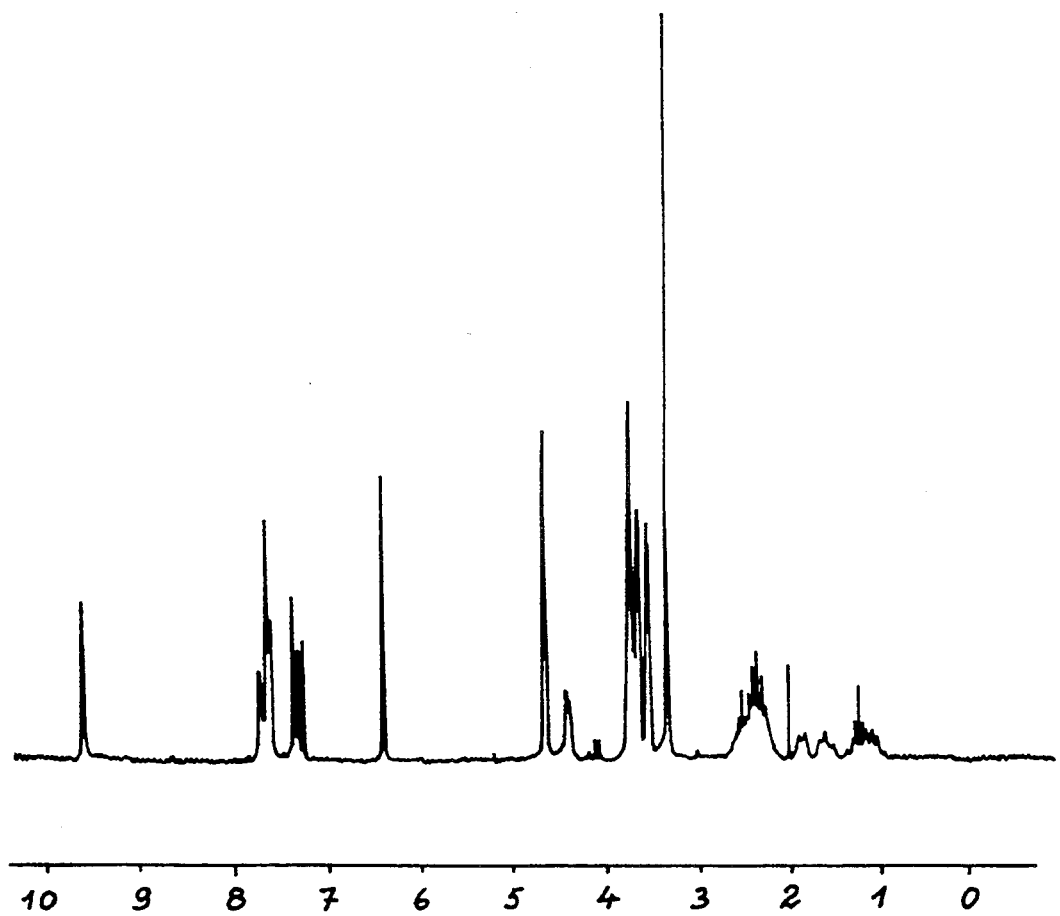

FIG. 33 shows the spectrum of the proton confirming the structure of the product obtained.

EXAMPLE 19

Preparation of N-carbobenzyloxy-α-benzylester γ-glutamyl-4-(2',5',8'-trioxanonyl)-7-coumarinylamide (compound 17) of formula

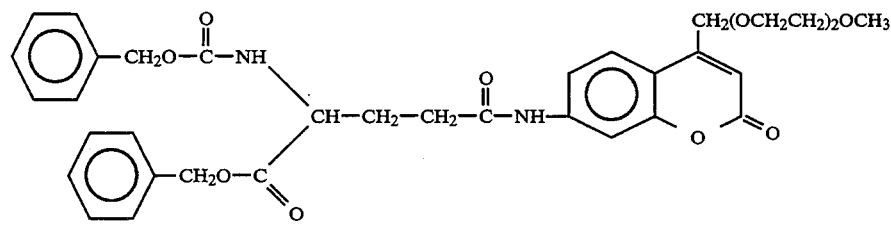

In this example compound 4 is coupled with α-benzylester of N-carbobenzyloxyglutamic acid.

In a 100 ml round-bottomed flask are dissolved 7.43 g (0.02 mole) of α-benzylester of N-carbobenzyloxyglutamic acid, 3.24 g of hydroxybenzotriazole, 5.87 g (0.02 mole) of compound 4 in 55 ml of dimethyl formamide. Cooling takes place to 5° C. and, accompanied by stirring, introduction of 4.13 g of dicyclohexyl carbodiimide DCCI (0.02 mole) takes place. After keeping at 5° C. for 1 hour, it is stirred for 20 h at ambient temperature, followed by filtering and elimination of the precipitate.

The solvent is evaporated in vacuo and taken up by 135 ml of a 5% bicarbonate solution and 200 ml of ethyl acetate. The organic phase is washed by 3×135 ml of 1N hydrochloric acid, 135 ml of 5% bicarbonate solution and 135 ml of water.

The organic solution is made dry and the product purified on a silica column using ethyl acetate as the eluent. Fractions 41 to 77 lead to 3.87 g (30%) of pure product.

The product has the following characteristics.

1°) TLC

Fluorescent silica K$_6$F; eluting solvent: ethyl acetate; developing at 254 and 356 nm (blue violet spot); Rf=0.45.

2°) NMR spectrum

Figure 34:
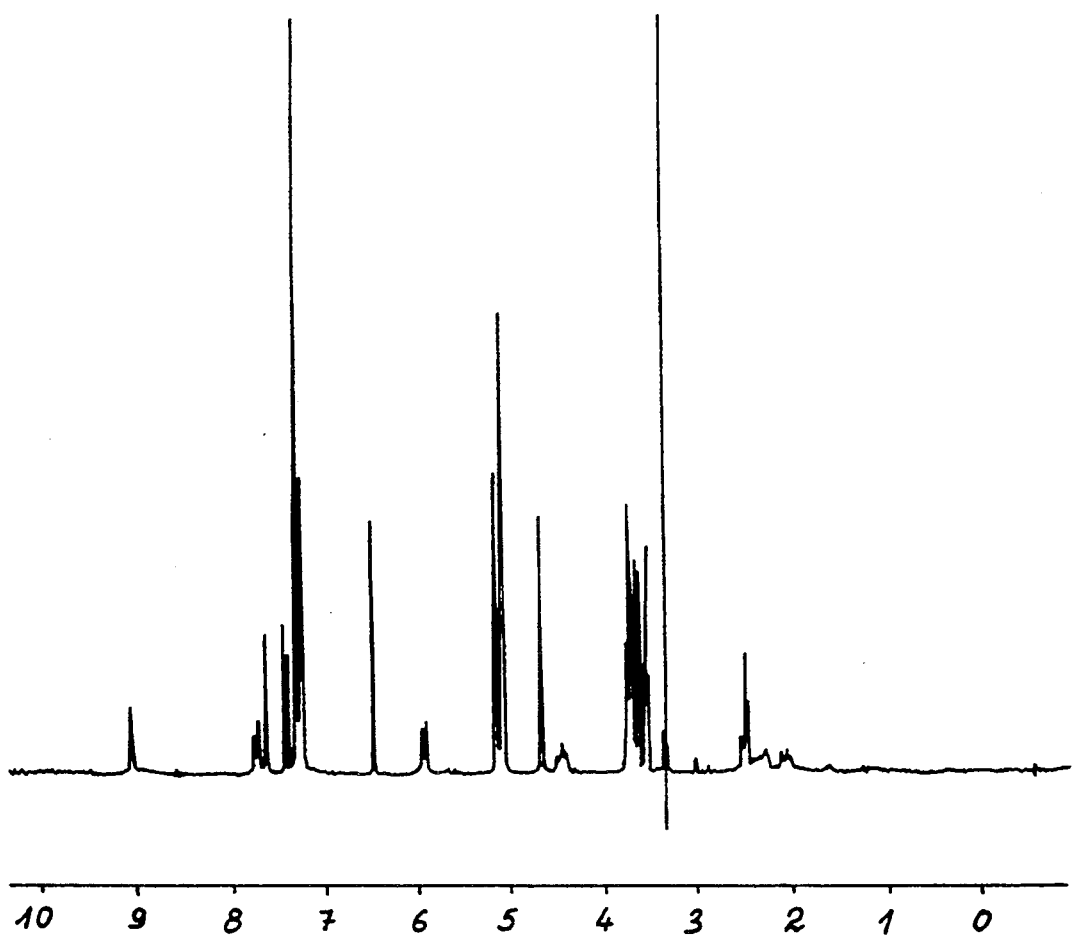

FIG. 34 shows the spectrum of the proton confirming the expected product structure.

EXAMPLE 20

Preparation of
γ-glutamyl-4-(2',5',8'-trioxanonyl)-7-coumarinylamide
(compound 18) of formula

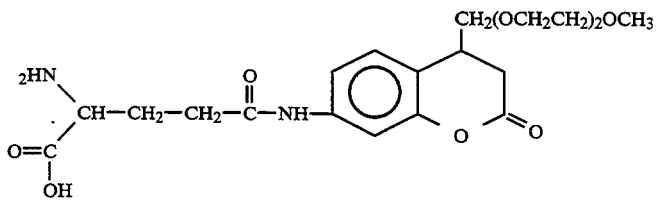

In this example, compound 17 is hydrogenated in solution in tetrahydrofuran.

Into a hydrogenating flask are introduced 114 ml of tetrahydrofuran, 3.82 g of compound 17 and 764 mg of palladium on 10% charcoal. Purging occurs with nitrogen and hydrogen is introduced. Stirring occurs for 8 h at atmospheric pressure and ambient temperature. After filtering the catalyst, the product which has crystallized in the catalyst is extracted by 2×400 ml of boiling methanol. The methanol is concentrated in vacuo to a volume of 100 ml. The product which crystallizes is centrifuged, rinsed once with methanol and dried in vacuo giving a yield of 1.55 g (65%.

The product has the following characteristics:

1°) TLC

Fluorescent silica K₆F; eluting solvent butanol/acetic acid/water 60:20:20; development at 254 and 356 nm (blue violet spot); Rf=0.35 (developed with ninhydrin).

2°) NMR spectrum

Figure 35:
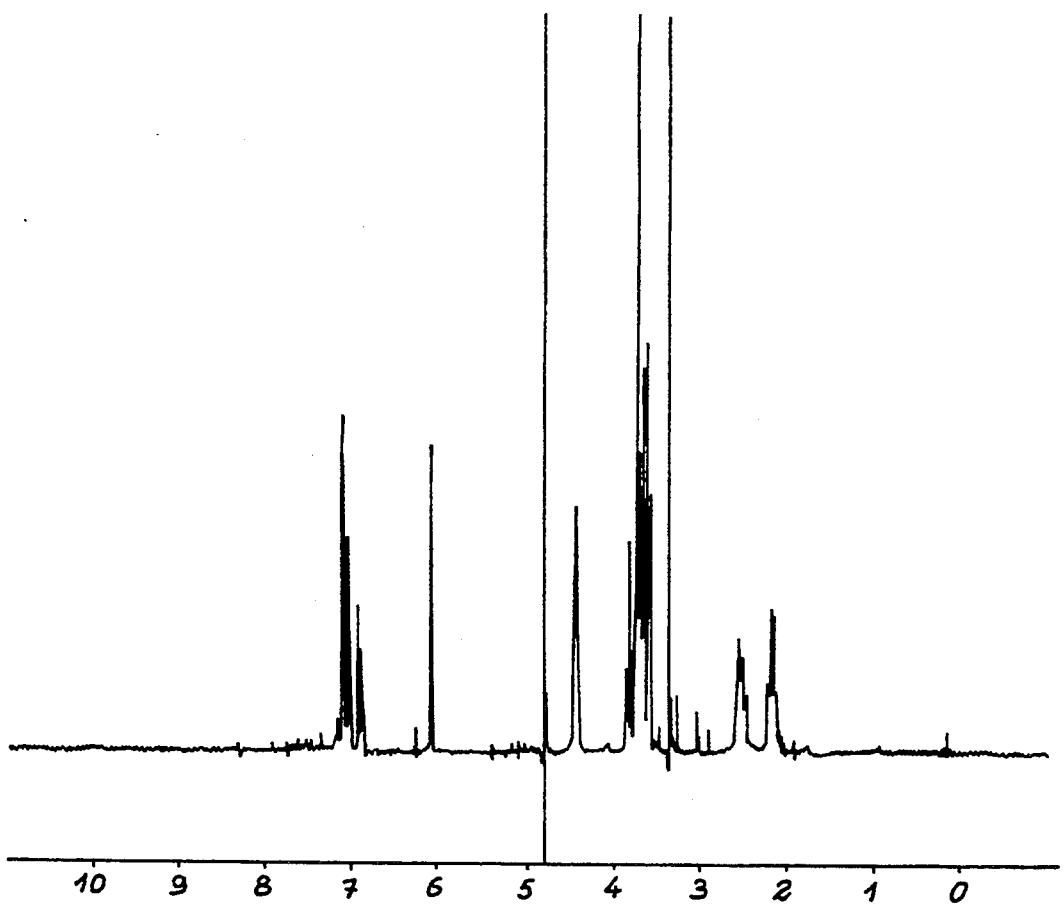

FIG. 35 gives the spectrum of the proton confirming the structure of the expected product.

3°) Mass spectrum (chemical ionization with ammonia).

Figure 36:
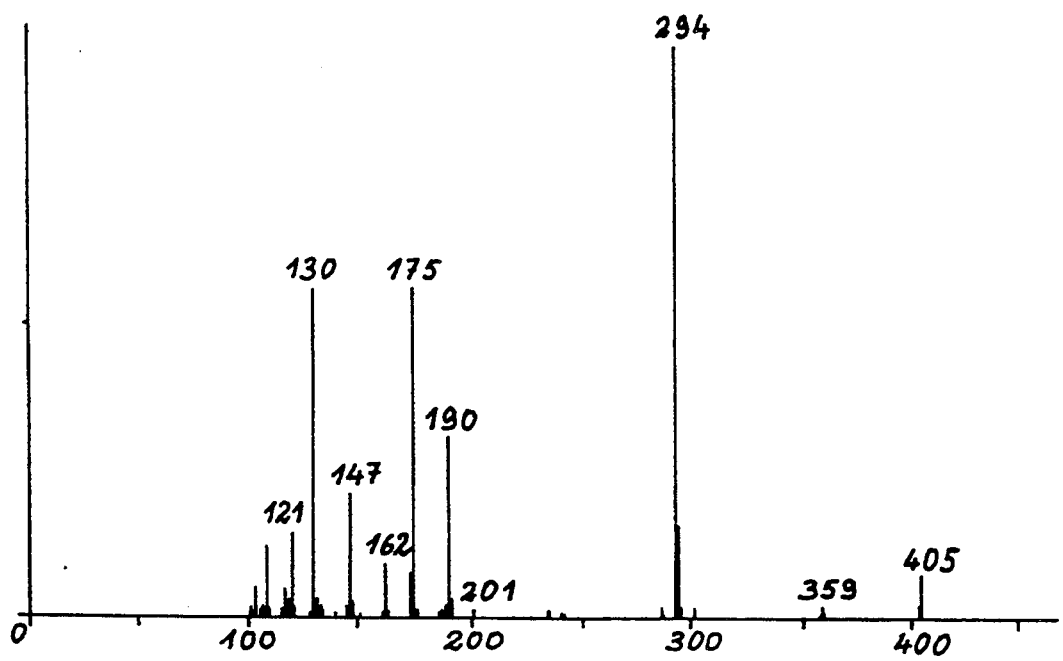

FIG. 36 gives the spectrum of the product obtained. There is a peak (M+1)=405 of the molecule and a peak at (293+1) of product 4 (fragmentation at the amide).

EXAMPLE 21

Preparation of ωFmoc α-Boc
L-lysyl-4-(2',5',8'-trioxanonyl)-7-coumarinylamide
(compound 19) of formula In a 50 ml round-bottomed flask are dissolved 2 g (4.27 mmole) of ω-Fmoc α-Boc-L-lysine and 1.25 g (4.27 mmole) of compound 4 in 15 ml of dimethyl formamide. Accompanied by stirring, introduction takes place of 0.881 g (4.27 mmole) of DCCI, followed by stirring for 20 h, filtration and precipitate elimination.

The solvent is evaporated in vacuo and the residue taken up by 40 ml of dichloromethane, followed by washing with 40 ml of 1N hydrochloric acid and twice 40 ml of water. Drying takes place on magnesium sulphate, followed by evaporation in vacuo.

The concentrate is purified by silica column chromatography using as the eluent a ternary mixture of n-butanol, ethyl acetate and cyclohexanone 30:20:30. On 65 10 ml fractions collected, fractions 51 to 65 are concentrated. Yield 1.52 g (48%).

The product has the following characteristics.

1°) mp=147° to 147.5° C.

2°) TLC.

Fluorescent silica K₆F: eluting solvent n-butanol/ethyl acetate/cyclohexanone 30:20:30; development at 254 and 356 nm (blue violet spot); Rf=0.63.

3°) NMR spectrum.

Figure 37:
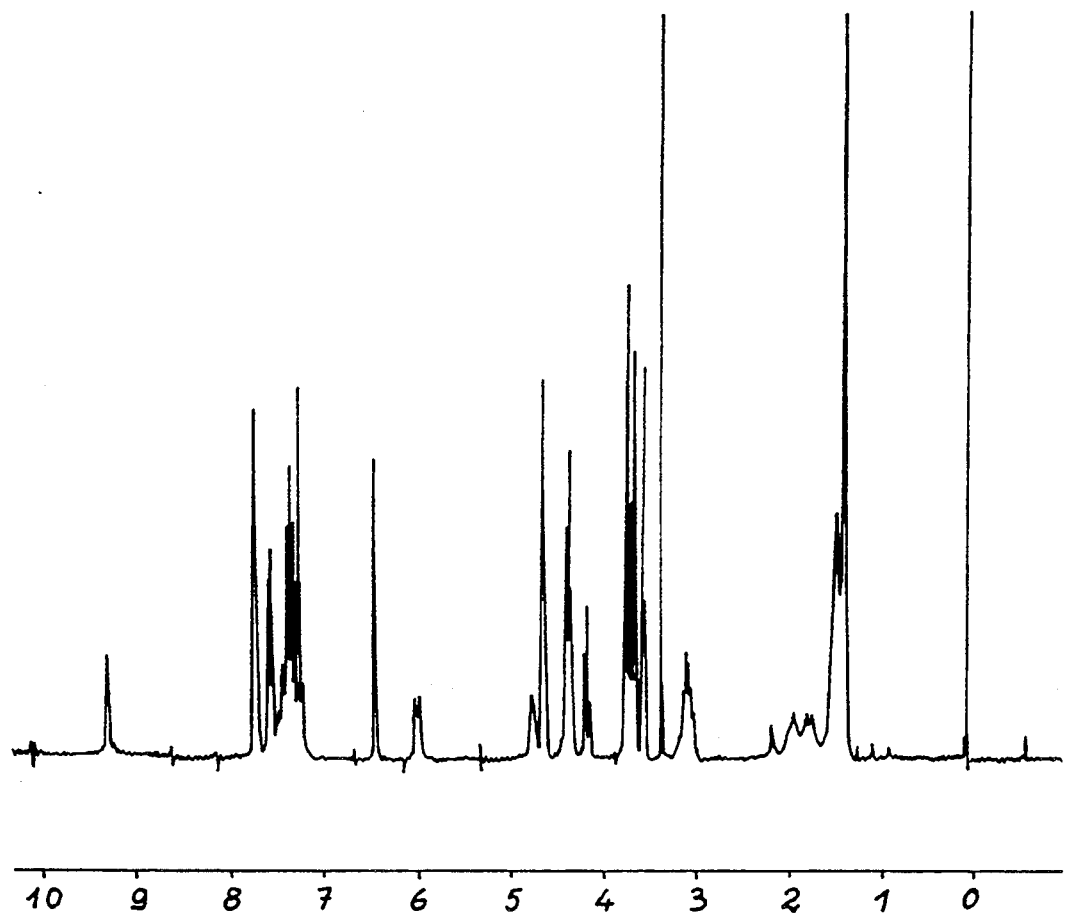

FIG. 37 shows the spectrum of the proton confirming the structure of the product obtained.

4°) Mass spectrum (chemical ionization with ammonia).

Figure 38:
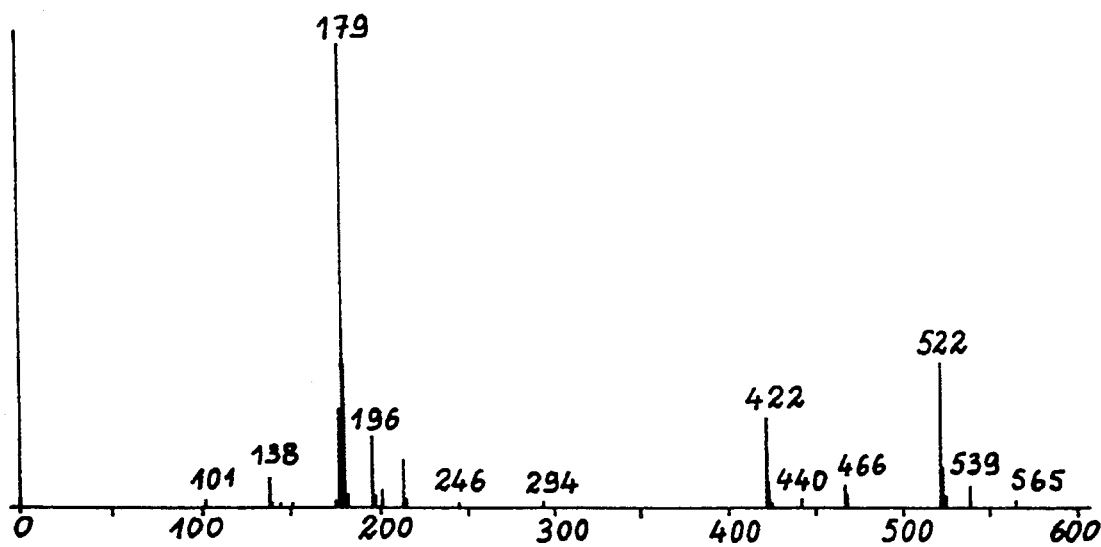

FIG. 38 shows the spectrum obtained. The peaks at 522 and 539 (522+17) confirm the mass of the product (743), which undergoes a fragmentation at the FMOC group (743-222+1).

In the examples given above, compounds 4, 10, 12 to 17 and 19 can be used as intermediates for the preparation of enzyme substrates, particularly polypeptides in the case of compounds 12 to 17 and 19. Compounds 13, 14, 16 and 18 can be used as enzyme substrates.

We claim:

1. Coumarin compound having the formula:

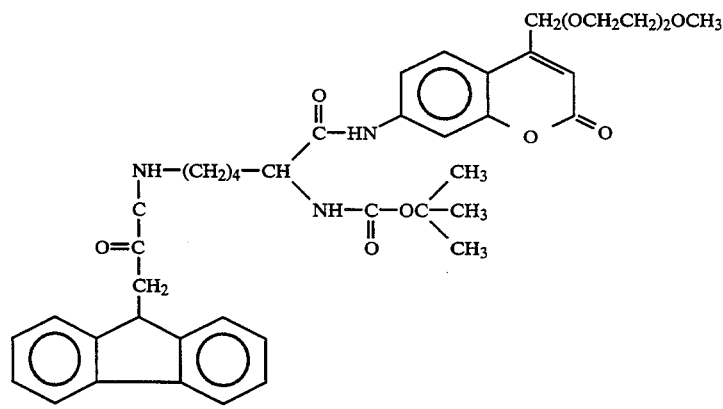

In this example compound 4 is coupled with ω-Fmoc α-Boc L-leucine using dicyclohexyl carbodiimide (DCCI) as the coupling agent.

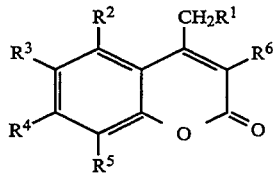

in which

1°) $R^1$ represents a substituent of the formulas

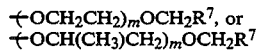

wherein m is an integer from 1 to 30 and $R^7$ represents a hydrogen atom, COOH, CONHNH$_2$, or COOR$^9$, with $R^9$ being $C_1$–$C_{10}$ alkyl, NH$_4$, or M$_{1/v}$ with M being a metal of valence v and $R^{10}$ being $C_1$–$C_{10}$ alkyl, 2°) $R^3$ represents a hydrogen atom, OH, or OR$^8$ with $R^8$ being $C_1$–$C_{10}$ alkyl, $R^4$ represents a hydrogen atom, NH$_2$, NHR$^8$ NR$^8$R$^{10}$, OH, or OR$^8$, and 4°) $R^2$, $R^5$, and $R^6$ each represents a hydrogen atom.

2. Coumarin derivative according to claim 1, wherein at least one of $R^3$ and $R^4$ represents NH$_2$, NHR$^8$, OH, or OR$^8$.

3. Coumarin derivative according to claim 2, wherein $R^4$ represents NH$_2$, NHR$^8$, or OH and represents a hydrogen atom.

4. Derivative according to claim 3, wherein $R^4$ represents NH$_2$, or OH.

5. Derivative according to claim 4, wherein $R^1$ represents (OCH$_2$CH$_2$)$_2$OCH$_3$ and $R^3$ represents a hydrogen atom.

6. Coumarin derivative according to claim 1, wherein $R^1$ represents (OCH$_2$CH$_2$)$_m$ OCH$_3$.

7. Coumarin derivative according to claim 6, wherein m is equal to 2.

8. Coumarin derivative according to claim 1, wherein at least one of $R^3$ and $R^4$ represents NHR$^8$ NR$^8$R$^{10}$, OH, or OR$^8$.

* * * * *